(12) United States Patent
Swain et al.

(10) Patent No.: US 6,507,757 B1
(45) Date of Patent: Jan. 14, 2003

(54) APPARATUS FOR ELECTRICAL STIMULATION OF THE BODY

(76) Inventors: Ian Douglas Swain, 1 Church Lane Lower Hemarton, Salisbury SF2 9NR (GB); Paul Nicholas Taylor, 8 Avon Meadows, Middle Woodford, Salisbury SP4 6NS (GB)

(*) Notice: Subject to any disclaimer, the term of this patent is extended or adjusted under 35 U.S.C. 154(b) by 34 days.

(21) Appl. No.: 09/652,081

(22) Filed: Aug. 31, 2000

(30) Foreign Application Priority Data

Jun. 20, 2000 (GB) .............................................. 0014968

(51) Int. Cl.$^7$ ................................................ A61N 1/36
(52) U.S. Cl. ...................................................... 607/49
(58) Field of Search ..................... 607/48, 49

(56) References Cited

U.S. PATENT DOCUMENTS

| | | |
|---|---|---|
| 4,796,631 A | 1/1989 | Grigoryev |
| 5,358,513 A | 10/1994 | Powell, III et al. |
| 5,546,681 A | 8/1996 | Goldston et al. |
| 5,643,332 A | 7/1997 | Stein |
| 5,746,499 A | 5/1998 | Ratcliffe et al. |
| 5,903,103 A | 5/1999 | Garner |
| 6,017,128 A | 1/2000 | Goldston et al. |
| 6,104,140 A | 8/2000 | Wut et al. |

OTHER PUBLICATIONS

JH Burridge et al., "Functional Electrical Stimulation: A review of the Literature Published on Common Peroneal Nerve Stimulation for the Correction of Dropped Foot" from *Review in Clinical Gerontology* 1998 (pp. 155–161).
W.T. Liberson et al. "Functional Electrotherapy: Stimulation of the Peroneal Nerve Synchronized with the Swing Phase of the Gait of Hemiplegic Patients" from *Archives of Physical Medicine & Rehabilitation* Feb. 1961 (pp. 101–105).

*Primary Examiner*—Scott M. Getzow
(74) *Attorney, Agent, or Firm*—Anthony R. Barkume, P.C.

(57) ABSTRACT

A stimulator for stimulating the leg or other parts of the body e.g. the leg in a patient with drop foot is provided, the stimulator being controlled by e.g a foot switch but being reliable in use and therefore commanding acceptance by users. The foot switch has to work in adverse environmental conditions and is subject to repeated use so that its characteristics vary with time. The invention provides a functional electrical stimulator for attachment to the leg that has adaptive characteristics and comprises first and second electrodes for attachment to the leg to apply an electrical stimulus, a foot switch for sensing foot rise or foot strike, a circuit responsive to said foot switch for generating stimulation pulses; and means forming part of said circuit for responding to changes in the resistance characteristics of said switch means by adjusting a corresponding response threshold of said circuit.

The invention also provides a two-channel stimulator that offers various possibilities for controlling the signals to be supplied to different muscle groups. For example, means may be provided defining a signal pathway between the first and second channels so that the supply of stimulation pulses in one of said first and second channels can be controlled by the state of switch means associated with the other of said first and second channels. In a further embodiment means defining a signal pathway between the first and second channels is arranged so that the supply of stimulation pulses in one of said first and second channels can be controlled by the state of activity of the other of said first and second channels. In a yet further embodiment the first channel has means arranged to cause the stimulation pulses to time-out after a predetermined period and the second channel having no or disabled timing means so that supply of stimulation pulses is continuous in a predetermined state of limb position responsive switch means associated with that channel. The two-channel stimulator can be used e.g., to treat bilateral dropped foot.

15 Claims, 20 Drawing Sheets

Asymmetrical biphasic waveform

Symmetrical biphasic waveform

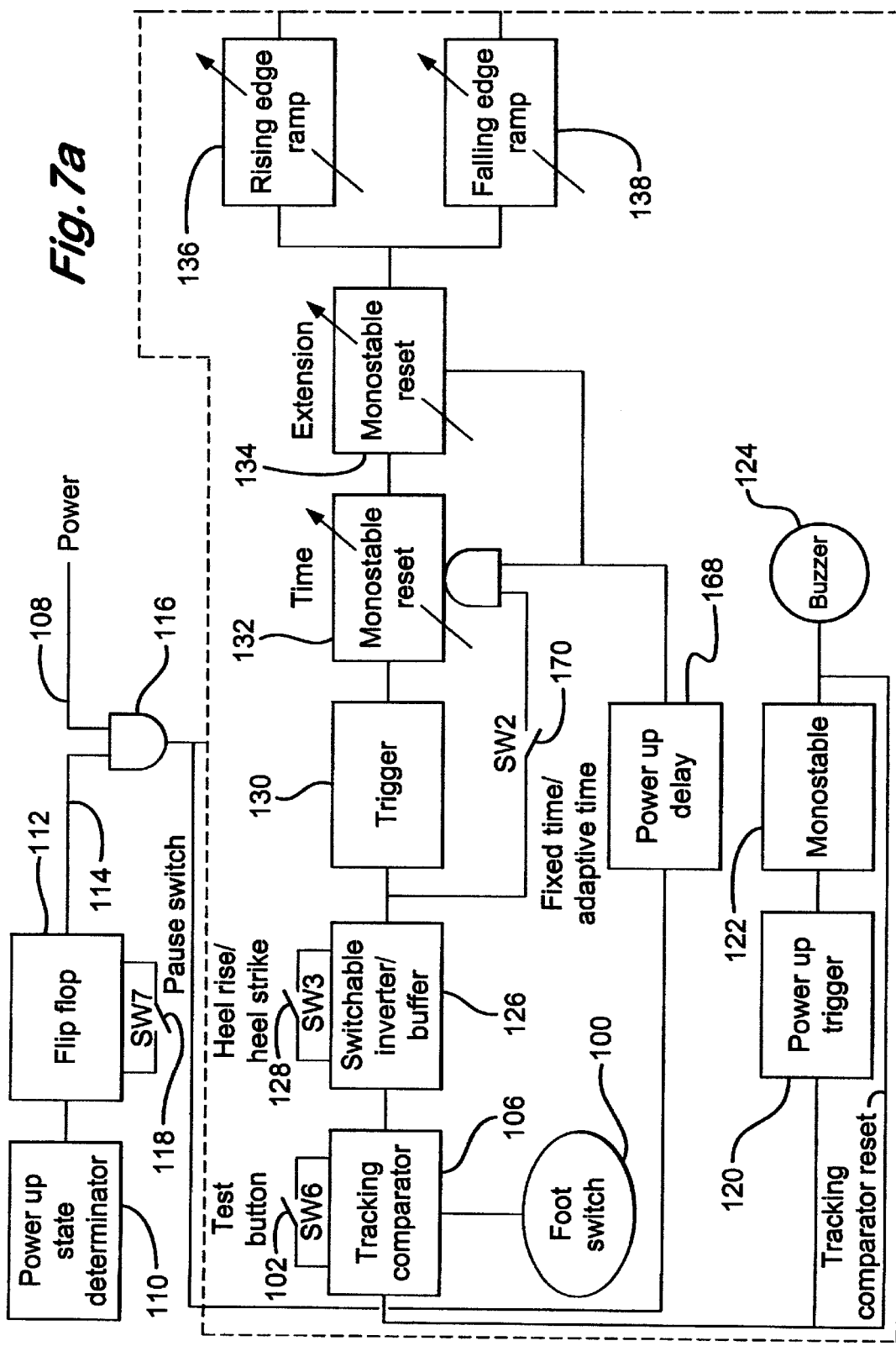

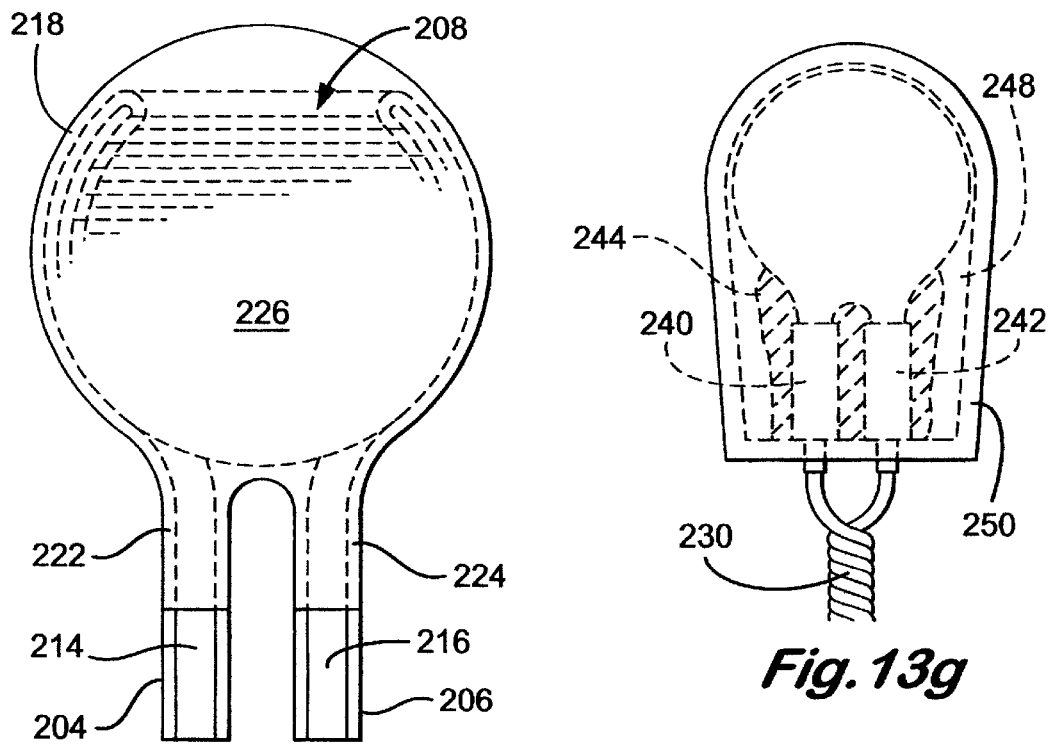
Fig. 13e
Fig. 13g
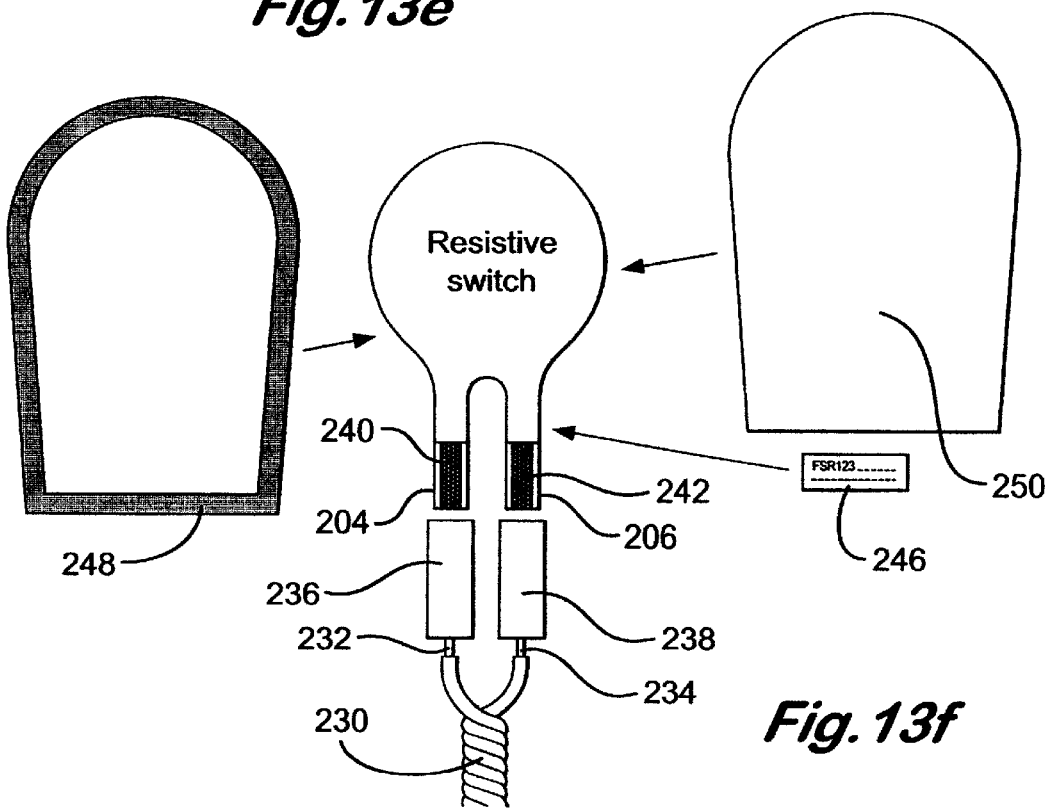
Fig. 13f

APPARATUS FOR ELECTRICAL STIMULATION OF THE BODY

FIELD OF THE INVENTION

The present invention relates to apparatus that a person can wear during walking to apply an electrical stimulus to his or her body and particularly, though not exclusively to his or her leg.

BACKGROUND TO THE INVENTION

The present invention provides apparatus for applying an electrical stimulus to a person's leg in timed relationship to leg movement during walking in order to achieve a benefit.

For example, a person who has a dropped foot is unable to lift his or her toes clear of the ground during the swing phase of walking. Such a problem is seen in people who have either a peripheral nerve lesion, as a result of trauma or disease, or an upper motor neuron lesion. It is the latter that responds to neuromuscular stimulation. Lesions of the lower motor neurons result in destruction of the neural pathway so that muscle contraction can be achieved only through direct stimulation of the muscle fibers.

The first reference to functional electrical stimulation (FES) is the work by Liberson et al, "Functional electrotherapy in stimulation of the peroneal nerve synchronized with the swing phase of gait of hemiplegic patients", *Arch Phys. Med. rehabil* 42, 202–205 (1961). At this time electrotherapy was commonplace, but functional electrotherapy was a new concept. Liberson defined it as follows: '. . . to provide the muscles with electrical stimulation so that at the very time of the stimulation the muscle contraction has a functional purpose, either in locomotion or in prehension or in other muscle activity. In other words, functional electrotherapy is a form of replacement therapy in cases where impulses coming from the central nervous system are lacking.'

Liberson used a portable stimulator to correct drop foot during walking. A train of pulses of 20–250 μsec duration, frequency 30–100 Hz and maximum peak current 90 mA was applied through conductive rubber electrodes. The negative (active) electrode was placed over the common peroneal nerve below the knee and the large indifferent electrode either on the thigh or on the lower leg. The stimulator was worn in the pocket and a heel switch was used to trigger the stimulus during the swing phase of the gait cycle. The switch was worn on the shoe on the affected side so that the electrical circuit was interrupted during the stance phase, when the weight was on the heel, and allowed to flow when the heel was lifted during the swing phase. Liberson was enthusiastic about the results, reporting that all the subjects experienced considerable improvement in gait. Despite improvements in the apparatus used, the basic idea of FES has remained unchanged. Sixteen papers on the topic published in the period 1960–1977 have been reviewed by J. H. Burridge et al, *Reviews in Clinical Gerontology*, 8, 155–161 (1998).

U.S. Pat. No. 5,643,332 (Stein) is also concerned with FES and explains that although variants of the technique have been tried and some success has been obtained, the most common appliance fitted to people with foot drop is an ankle-foot orthosis (AFO) which is a plastics brace that fits around the lower leg and holds the foot at close to a 90° angle with respect to the long axis of the leg, and which does not employ electrical stimulation. Stein gives a number of reasons why FES had not replaced the AFO, amongst which is unrehability of the foot switch. In order to overcome this problem, Stein proposes a tilt sensor for measuring the angular position of the lower leg, although he also provides a socket for a hand or foot switch for those patients who cannot use a tilt sensor as there is insufficient tilt of the lower leg. A muscle stimulator for knee stabilization, also based on a tilt switch, is disclosed in U.S. Pat. No. 4,796,631 (Grigoryev). Muscle stimulation for the treatment and prevention of venous thrombosis and pulmonary embolism is disclosed in U.S. Pat. No. 5,358,513 (Powell III).

Footwear with flashing lights controlled by pressure switches is known, see U.S. Pat. Nos. 5,546,681, 5,746,499 and 6,017,128 (L.A. Gear, Inc.), U.S. Pat. No. 5,903,103 (Gamer) and U.S. Pat. No. 6,104,140 (Wut).

SUMMARY OF THE INVENTION

It is an object of the invention to provide a stimulator controlled by a foot switch that is more reliable in use and therefore commands wider acceptance by users.

It is also an object of the invention to provide a circuit for triggering by a pressure switch subject to repeated use and/or adverse environmental conditions which adapts to changes of switch characteristics with time.

The invention provides a functional electrical stimulator for attachment to the lower leg comprising;

first and second electrodes for attachment to the leg to apply an electrical stimulus;

a foot switch for sensing foot rise or foot strike;

a circuit responsive to said foot switch for generating stimulation pulses; and means forming part of said circuit for responding to changes in the resistance characteristics of said switch means by adjusting a corresponding response threshold of said circuit.

The electrodes and the Coot switch are removably connected by e.g. plug and socket connectors to a body of the apparatus in which batteries and an electrical control circuit are housed. The invention also covers the control circuit without the electrodes and foot switch in place. Thus the invention further provides electrical apparatus for connection as part of a functional electrical stimulator for a leg, said apparatus comprising:

means providing a removable connection for first and second electrodes that in use are attached to the leg to apply an electrical stimulus;

means providing a removable connection for a foot switch for sensing foot rise or foot strike;

a circuit for responding to said foot switch for generating stimulation pulses; and means forming part of said circuit for responding to changes in the resistance characteristics of said switch by adjusting a corresponding response threshold of said circuit.

The invention also provides an electrical stimulator for attachment to the body comprising:

first and second electrodes for attachment to the body to apply an electrical stimulus;

switch means which passes between on and off states on application and removal of load;

a circuit responsive to said switch means for generating stimulation pulses; and means forming part of said circuit for responding to changes in the resistance characteristics of said switch means by adjusting a corresponding response threshold of said circuit.

It is a further object of the invention to provide electrical stimulation apparatus that may be applied to the body to achieve effective control of discrete muscle groups.

In the case of a single channel stimulator, for example, that is used to control dropped foot problems remain in some users that control of the ankle, knee or hip joint may be desirable. Lack of knee flexion on swing through can give difficulty in ground clearance despite adequate dorsiflexion. Lack of plantar flexion and hip extension control prevents the acceleration effect of the terminal stance phase of gait. Quadriceps weakness can cause rapid fatigue, reducing the distance that users can walk. Lack of hip abduction due to poor control ofd the gluteus medialis can lead to a scissirs gait. Balance while walking can be significantly reduced by the absence of contra-lateral arm swing.

The above problems can be addressed, according to the invention, by stimuation of a selected second group of muscles at appropriate times duing the gait cycle.

In one aspect the invention provides an electrical stimulator for attachment to the body comprising:

first and second channels for supplying stimuli to discrete muscle groups, each channel having first and second electrodes for attachment to the body to apply an electrical stimulus to a respective muscle group aid a circuit for supplying stimulation pulses to said electrodes;

at least one switch means responsive to limb position for controlling the supply of stimulation pulses in at least one channel; and means defining a signal pathway between the first and second channels so that the supply of stimulation pulses in one of said first and second channels can be controlled by the state of switch means associated with the other of said first and second channels. In the above stimulator, supply of the stimulation pulses via the first channel may be arranged to be initiated by change in state of a switch associated with the second channel and is arranged to be ended by change in state of a switch associated with the first channel.

A further form of the invention provides an electrical stimulator for attachment to the body comprising:

first and second channels for supplying stimuli to discrete muscle groups, each channel having first and second electrodes for attachment to the body to apply an electrical stimulus to a respective muscle group and a circuit for supplying stimulation pulses to said electrodes;

at least one switch means responsive to limb position for controlling the supply of stimulation pulses in at least one channel; and means defining a signal pathway between the first and second channels so that the supply of stimulation pulses in one of said first and second channels can be controlled by the state of activity of the other of said first and second channels. In the above stimulator, change in state of switch means associated with the first channel may be arranged to initiate supply of the stimulation pulses in the first channel, and the signal pathway between the channels may include delay means so that supply of pulses in the first channel initiates supply of pulses in the second channel with a delay.

In a yet further form of the invention, an electrical stimulator for attachment to the body is provided that comprises:

first and second channels for supplying stimuli to discrete muscle groups, each channel having first and second electrodes for attachment to the body to apply an electrical stimulus to a respective muscle group and a circuit for supplying stimulation pulses to said electrodes; at least one switch means responsive to limb position for controlling the supply of stimulation pulses in at least one channel; and means for controlling the supply of stimulation pulses in the second channel, said means being selected from (a) second switch means which changes state on the application of pressure and (b) connections to the first channel for supplying to said second channel a signal indicative of the state of the first channel.

Another alternative form of the invention provides an electrical stimulator for attachment to the body comprising:

first and second channels for supplying stimuli to discrete muscle groups, each channel having first and second electrodes for attachment to the body to apply an electrical stimulus to a respective muscle group and a circuit for supplying stimulation pulses to said electrodes;

at least one switch means responsive to limb position for controlling the supply of stimulation pulses in at least one channel;

the first channel having means arranged to cause the stimulation pulses to time-out after a predetermined period and the second channel having no or disabled timing means so that supply of stimulation pulses is continuous in a predetermined state of limb position responsive switch means associated with that channel.

The above apparatus may take the form of a two-channel stimulator in order to address the problem of dropped foot and stimulate a further muscle group, e.g. the gluteus maximus, calf muscle or hamstring. Trials have shown that walking speed and physiological cost index are improved when either calf or hamstrings are stimulated in addition to common peroneal stimulation. The apparatus may also be used to treat bilateral dropped foot.

The invention also provides methods for the treatment of patients using the above two-channel apparatus.

In a further aspect the invention provides a pressure-sensitive resistor useable as a foot switch to be located in, on or under a shoe insole, said switch having an active portion comprising an array of fingers in contact with a conductive pad so that mechanical pressure urging the pad towards the fingers reduces the resistance of the switch, the fingers being of a first conductive material and having leads also of said first conductive material, said leads being covered by a second conductive material.

The invention also provides in combination the above mentioned stimulation apparatus and the above mentioned pressure switch.

BRIEF DESCRIPTION OF THE DRAWINGS

The invention will now be further described, by way of example only, with reference to the accompanying drawings, in which:

FIGS. 13a–13g show successive stages in the manure of a resistive switch that form part of a further aspect of the invention.

DETAILED DESCRIPTION OF PREFERRED EMBODIMENT

Figure 1:
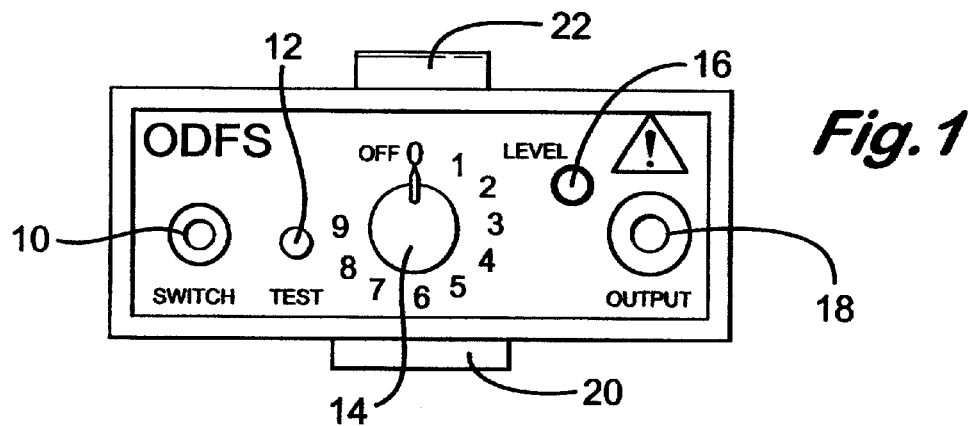
FIG. 1 is a view of a front panel of an electrical nerve stimulator according to the invention.

The apparatus disclosed in the drawings is an electronic device designed to assist people who have a dropped foot due to neurological damage that inhibits walking. As previously explained, a dropped foot, the inability to lift a foot whilst walking, resulting in the foot being dragged forward or swung out to the side, is a common disability following neurological injury. By stimulating the common peroneal nerve at its most superficial point, passing over the head of the fibula bone, it is possible through excitation of the withdrawal reflex to cause dorsiflexion with degrees of hip and knee flexion. If this is timed with walking using a foot switch worn in the shoe, walking can be significantly improved. The stimulus gives rise to a sensation like "pins and needles" and the patient soon becomes used to it. The apparatus can be made about the same size as a stack of playing cards, and it can be worn in the pocket or on a belt clip. Wires worn under the clothing carry the electrical stimulus to self-adhesive skin surface electrodes on the side of the leg. A small foot switch is placed in the shoe under the heel. The apparatus can be used as an assistive aid or as a training device to strengthen the muscles and achieve voluntary control. Additionally the device has a role in physiotherapy gait re-education, allowing isolated components of the gait cycle to be practiced under the supervision of a therapist.

The front panel of the device is shown in FIG. 1 and has a number of sockets and controls for the user. A jack socket 10 is provided for a foot switch. An output test button 12 enables electrode positions to be tested by the therapist and by the user and can be used by the therapist when the stimulator is being used during exercising to practice components of gait. An output is given when the button is pressed when the apparatus is being used in heel strike mode or when the button is released if it is being used in heel rise mode. The test button will not operate if weight is on the foot switch. A combined stimulation level and on/off switch 14 enables the contraction strength to be controlled by adjusting the stimulation puke width from 3 to 350 $\mu$s. An output indicator LED 16 flickers when the apparatus has been triggered. An electrode jack socket 18 of size different from the foot switch socket 10 is provided. A pause switch 20 is provided that when pressed puts the apparatus into sleep mode, which is required when the user sits down. To return the apparatus to its active state, the user need only press the switch 20 again. A bleep is heard, and then the apparatus again responds to the foot switch. A belt clip 22 also appears in the drawing.

The apparatus also has a number of controls that are set by the therapist and are not normally accessible to the user.

Figure 2:
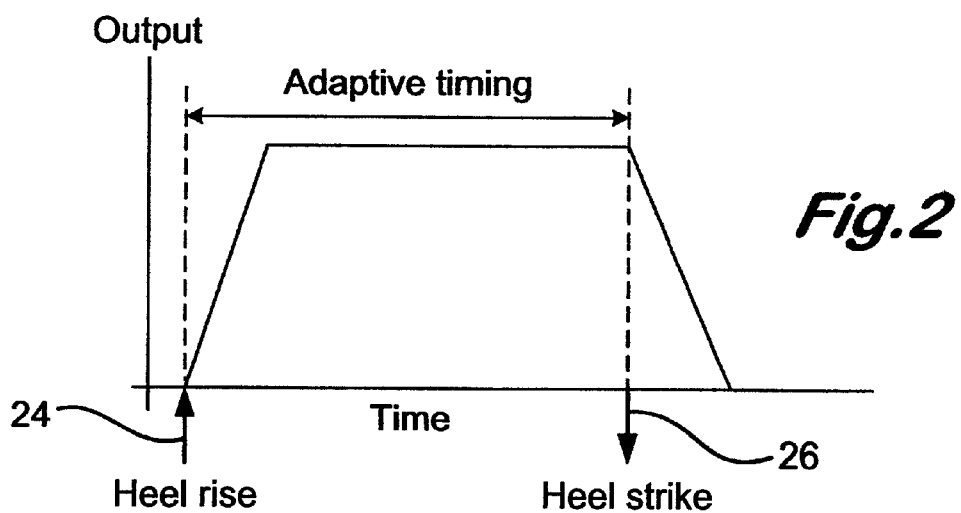
FIG. 2 is a graph showing stimulation envelope against time for the apparatus in foot rise and foot strike modes and in an adaptive timing mode.
Figure 3:
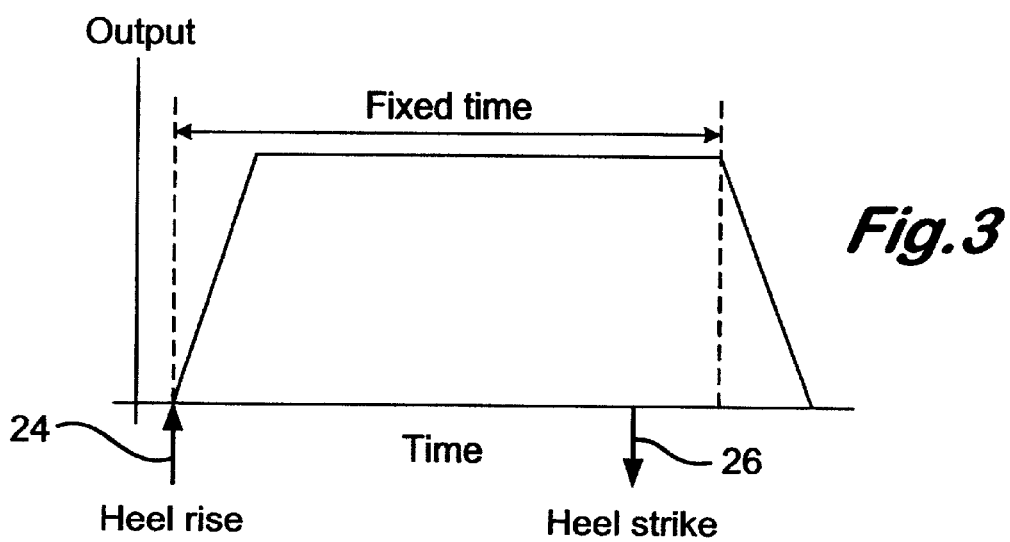
FIGS. 3 and 4 are graphs similar to that of FIG. 2, but with the apparatus in a fixed time mode and in an extension mode respectively.
Figure 4:
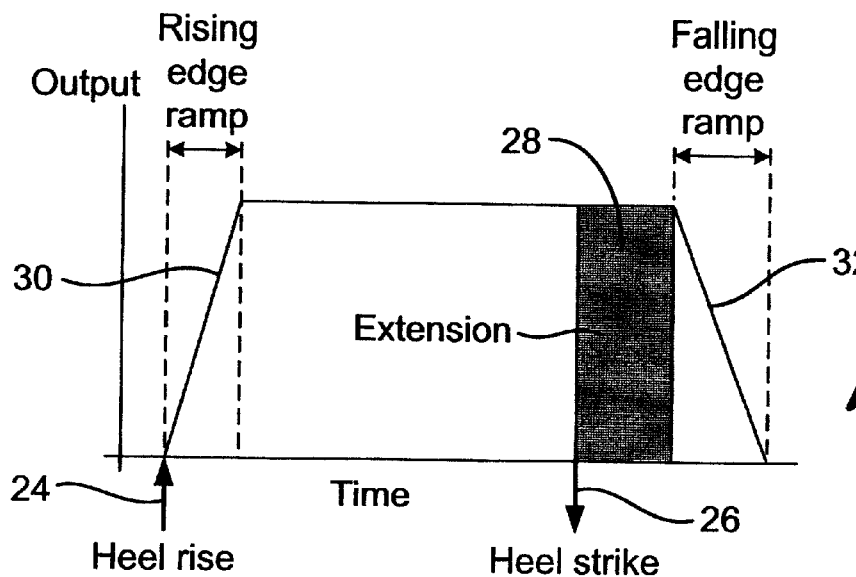

A heel rise/heel strike selection switch 128 (FIG. 7a) determines whether the apparatus is triggered when pressure is placed on the foot switch or when it is released from the foot switch, the signal in the heel rise mode being shown in FIG. 2, the times of heel rise and heel strike being shown by the arrows 24, 26. A fixed time/adaptive time mode switch 170 determines how the apparatus responds to a triggering event. In one position the stimulation envelope of the apparatus is maintained as long as pressure is applied to the foot switch (up to a maximum time out) when the apparatus is in the heel strike mode, or is maintained as long as pressure is released when the apparatus is in heel raise mode. In this way the stimulation envelope can adapt to the speed of the patients walling, and a stimulation envelope for this mode is shown in FIG. 2. In the other position of the switch 170 the apparatus is triggered for a predetermined time set by a time control, the duration of the resulting stimulation envelope being independent of interval between heel rise and heel strike 24,26 as shown in FIG. 3. The duration of the stimulation envelope from the apparatus when it is operating in the fixed time mode is determined by a time control 132 and is, for example, variable from 0.5 sec to 6 seconds. An extension control 134 is provided to cause the stimulation envelope of the apparatus to be maintained after e.g. heel strike has occurred to end contraction. The extension period can be adjusted within the range e.g. 0–1.5 seconds and can be used to prevent the user's toes from rapidly striking the ground after heel strike by providing a braking action from the tibialis anterior, EMG studies have shown this to be a closer approximation to normal gait. The stimulation envelope is shown in FIG. 4, the output period beyond heel strike 26 being the shaded area 28. Rising edge ramp and falling edge ramp controls 136, 138 respectively determine the time needed for the stimulation envelope to reach its maximum level after initiation and to fall to zero at the end of stimulation, which are represented in FIG. 4 by the slopes of ramps 30, 32.

Figure 5A:
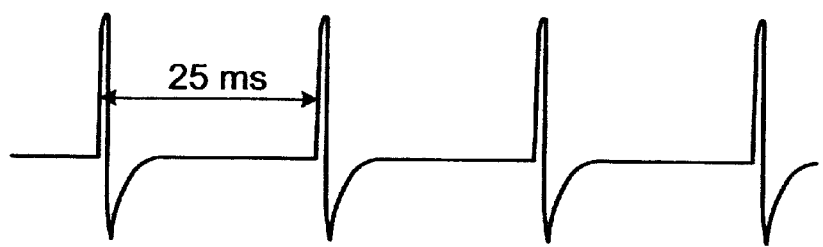
FIGS. 5a and 5b show alternative pulse waveforms for an output pulse train produced by the apparatus.
Figure 5B:
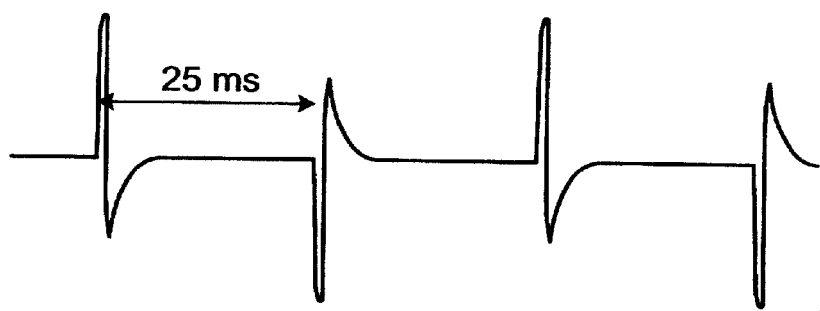

A control for output current enables it to be adjusted within a range of e.g. 15 mA to 100 mA. The output is a train of pulses that may be monophasic (monopolar) or biphasic (bipolar). For example, in one position of switch 158 (FIG. 7b) the apparatus provides an asymmetrically biphasic wave form as shown in FIG. 5a, and in the other position the apparatus provides a biphasic waveform as shown in FIG. 5b, this form reducing the risk of electro-chemical skin irritation due to ion migration. However the biphasic waveform produced by the present circuit produces a maximum amplitude of stimulation that is reduced by 25% compared to the monophasic waveform, resulting in a weaker maximum contraction, and it does not allow the use of electrode positions that exploit the effects of electrode polarity, for example in common peroneal stimulation. The bi-phasic waveform is therefore used mainly with patients who are at high risk of skin irritation.

Electrical pulses applied to the body via skin surface electrodes cause depolarization of the underlying nerve membrane, which causes the propagation of an impulse along the nerve and contraction of the associated muscle. The response of the nerve depends on the properties of the applied stimulus. If the stimulus is too short, high stimulus amplitude is required to bring about depolarization, and the amplitude of the stimulus required can be reduced by increasing the threshold, but only up to a maximum. The most efficient length of impulse is about 300 $\mu$s with little decrease in threshold beyond 1 ms, the required currents being about 15–150 mA. A chain of pulses is required to produce a fused tetanic contraction. As the pulse repetition frequency is increased, the individual contractions of the muscles being stimulated become closer together until at about 10 Hz fused contraction is achieved. However, the user will still be aware of vibration due to the individual pulses. By about 20 HZ vibration is reduced and a frequency of 30–40 Hz avoiding the user becoming aware of individual pulses while not resulting in rapid muscle fatigue. A frequency of 40 Hz is suitable for eliciting reflectors. An appropriate frequency can be selected for individual patients. By slowing the rising and falling edges of the stimulation envelope, the stimulus can be made more comfortable for the patient, a ramp time of 1–2 s being suitable but some users with severe spastisity requiring a ramp time of 6s or above.

Figure 6A:
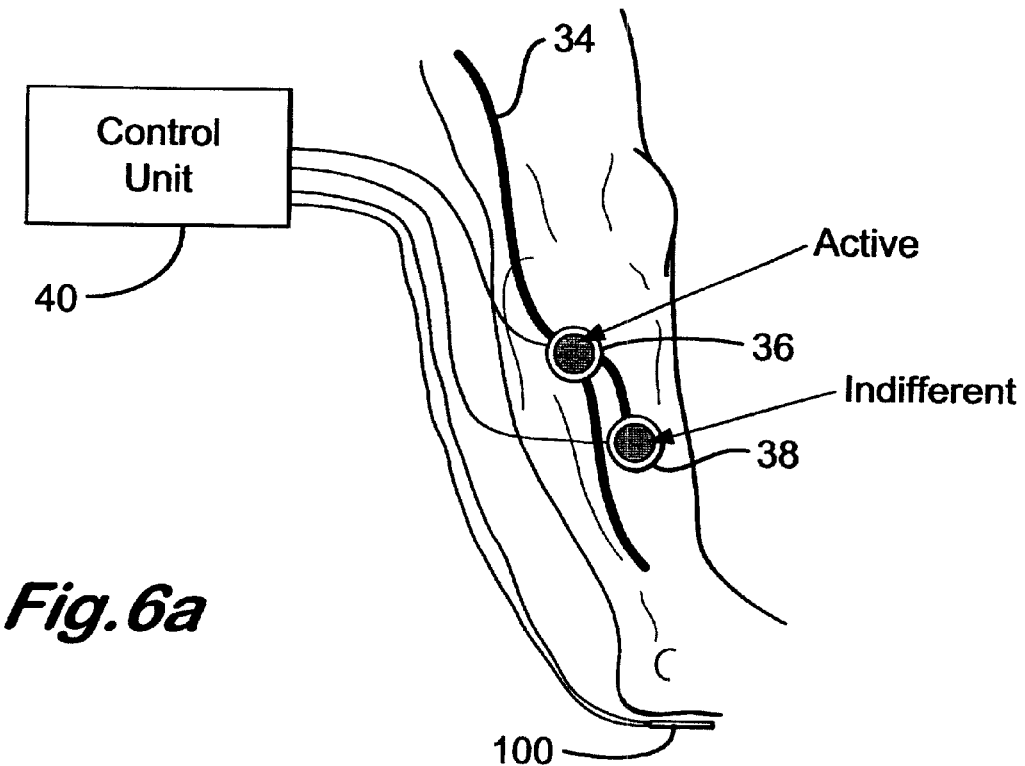
FIGS. 6a and 6b show the apparatus applied to the leg with the electrodes in alternative positions.
Figure 6B:
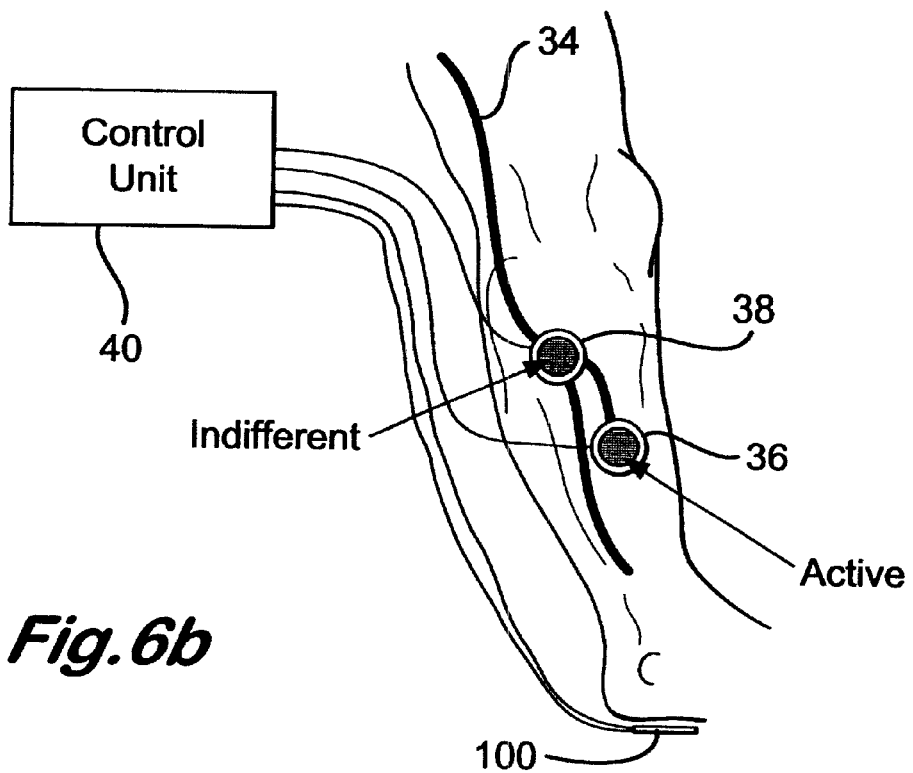

One way in which the apparatus can be applied to the user's leg is shown diagrammatically in FIGS. 6a and 6b. The peroneal nerve 34 passes just under the head of the fibula and bifurcates to form deep and superficial branches. An active electrode 36 may be placed over the common peroneal nerve just below the head of the fibula, and an indifferent electrode is located about 5 cm below and slightly medially of the active electrode over the motor point of the anterior tibialis, as seen in FIG. 6a. This is a standard position to produce a flexion withdrawal response. In FIG. 6b the positions of the active and indifferent electrodes are reversed, and in this arrangement in some cases eversion can be decreased while still producing dorsiflexion. The foot switch 100 and the electrodes 36, 38 are connected to a control unit 40 that includes the above described front panel and the circuitry described below.

The foot switch 100 comprises a force-sensitive resistor whose resistance reduces from a maximum of about 2MΩ to a minimum of about 2 kΩ when force is applied to it. The inventors have realized that the parameters of the foot switch change with time, especially in the harsh environment of a show where they are exposed to warmth and moisture and are subject to loads of about 100 Kg that in use are applied and removed typically over $10^4$–$10^6$ cycles. An ordinary potential divider and comparator when used lo determine the state of the switch give unreliable results. and it is necessary to use a tracking comparator, where the reference voltage across a capacitor, charged through a resistor from a force sensitive resistor potential divider. The voltage on the capacitor changes with voltage from the potential divider, but with a delay. Hysteresis is used to prevent jitter around the switching point Consequently the switching reference voltage sits just below the potential divider voltage when it is high and just above when the potential divider voltage is low. Reliable switching can be obtained over a large range of resistance changes in the force sensitive resistor. The reference voltage can be rapidly set when the apparatus is switched on or taken out of sleep mode.

Figure 7:
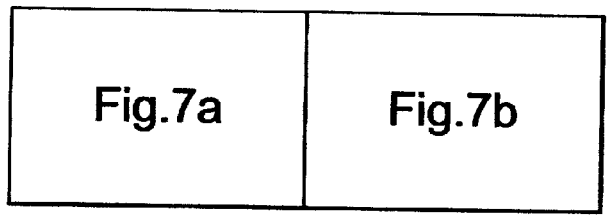
FIGS. 7a and 7b combine together to form a block diagram of the electrical nerve stimulator.
Figure 8:
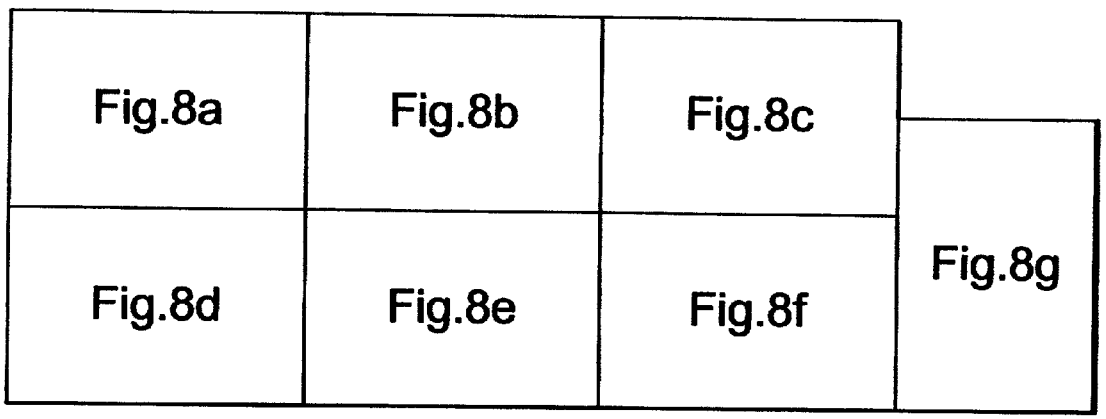
FIGS. 8a, 8b, 8c, 8d, 8e, 8f and 8g combine together to form a circuit diagram corresponding to the block diagram of FIG. 7.
Figure 12:
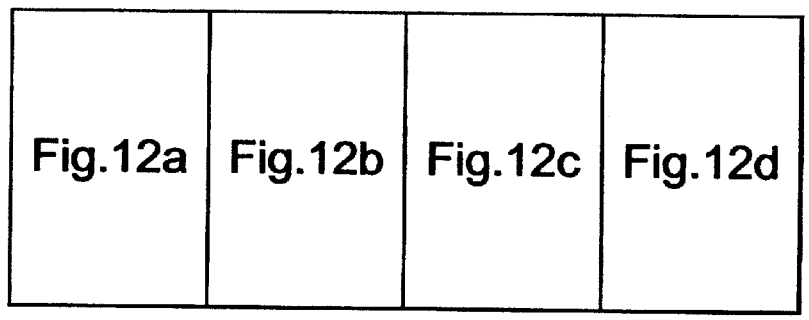
FIGS. 12a, 12b, 12c and 12d combine together to from a block diagram of a two-channel nerve stimulator.
Figure 7B:
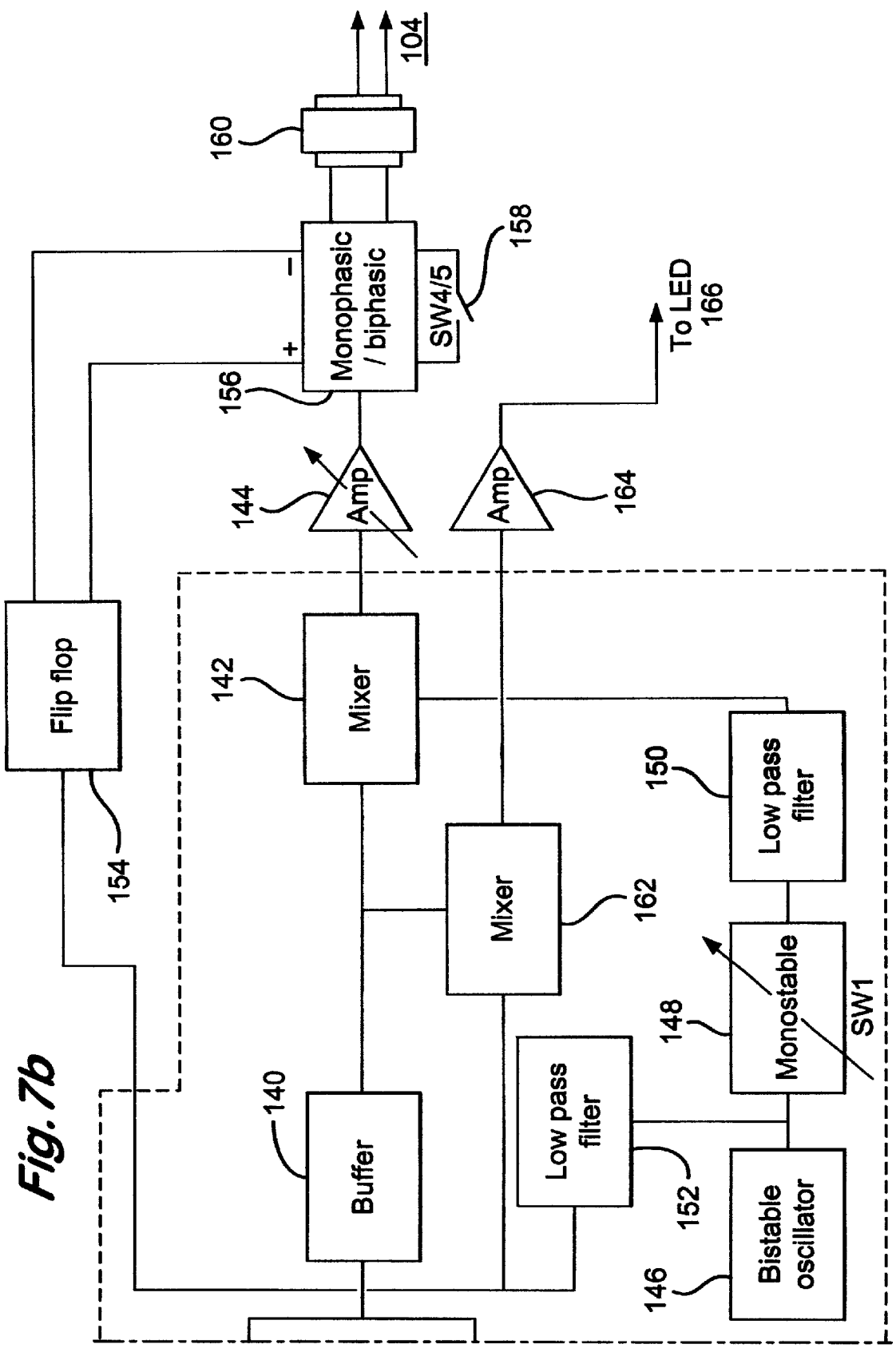
Figure 8A:
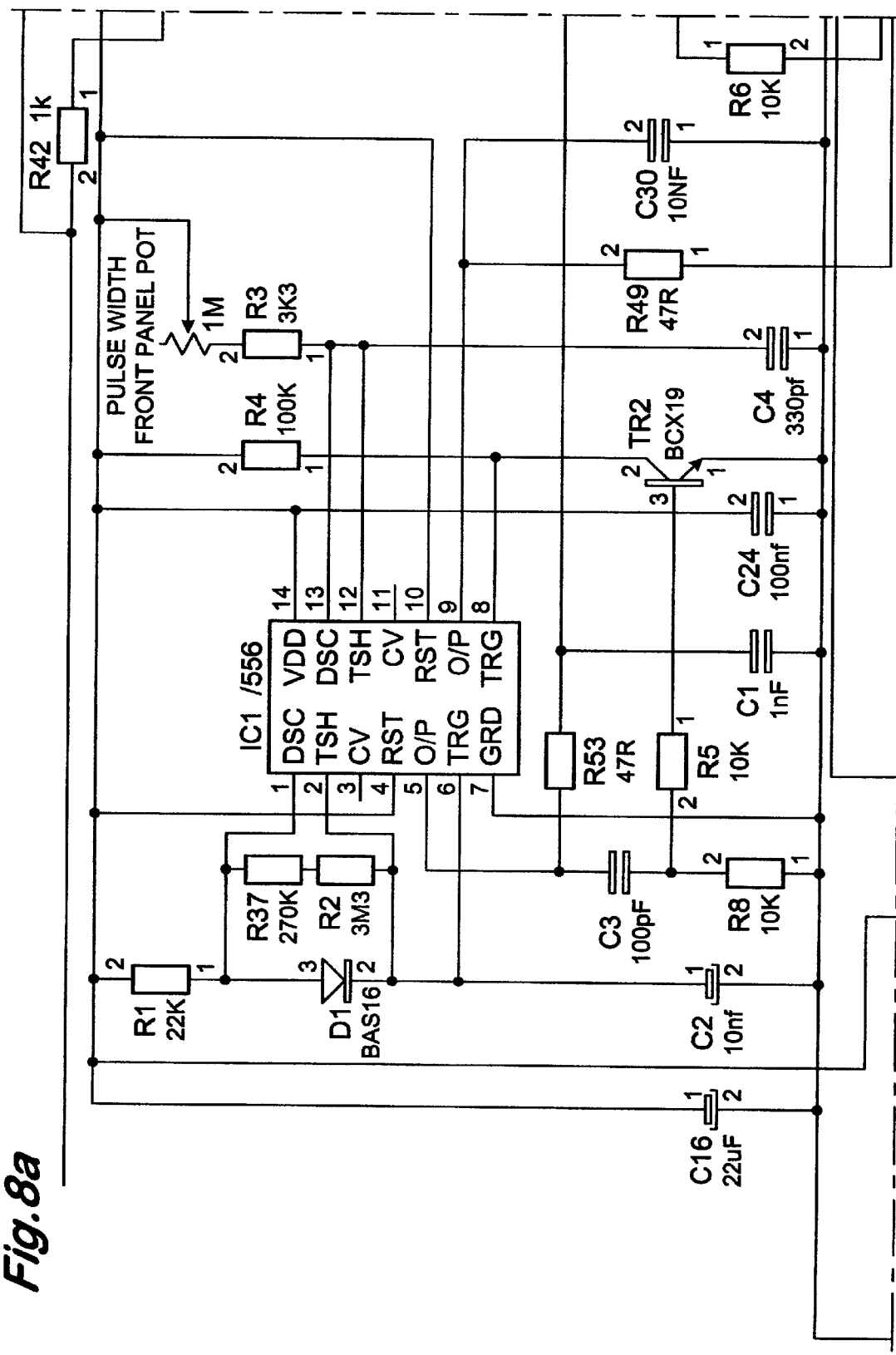
Figure 8B:
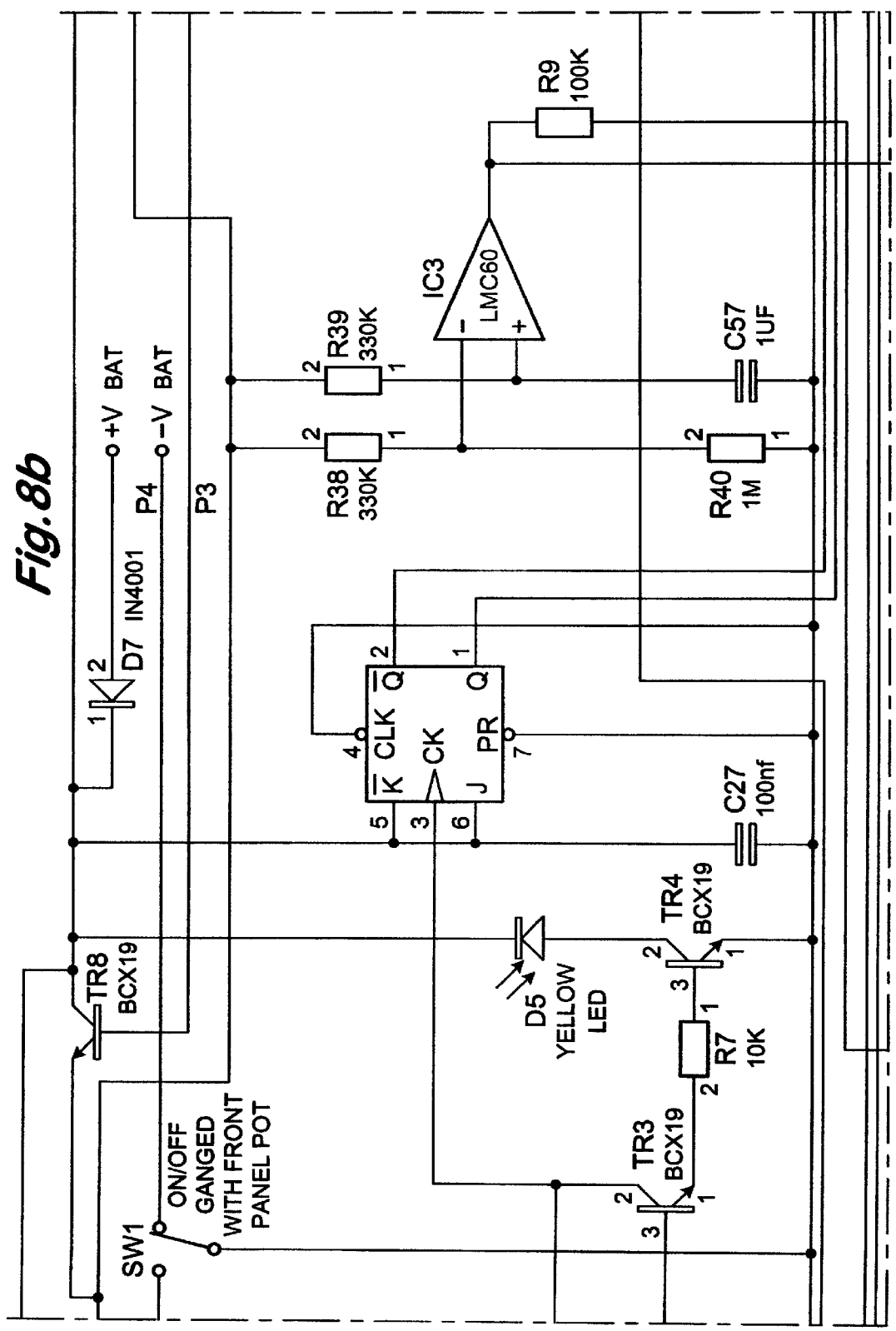
Figure 8C:
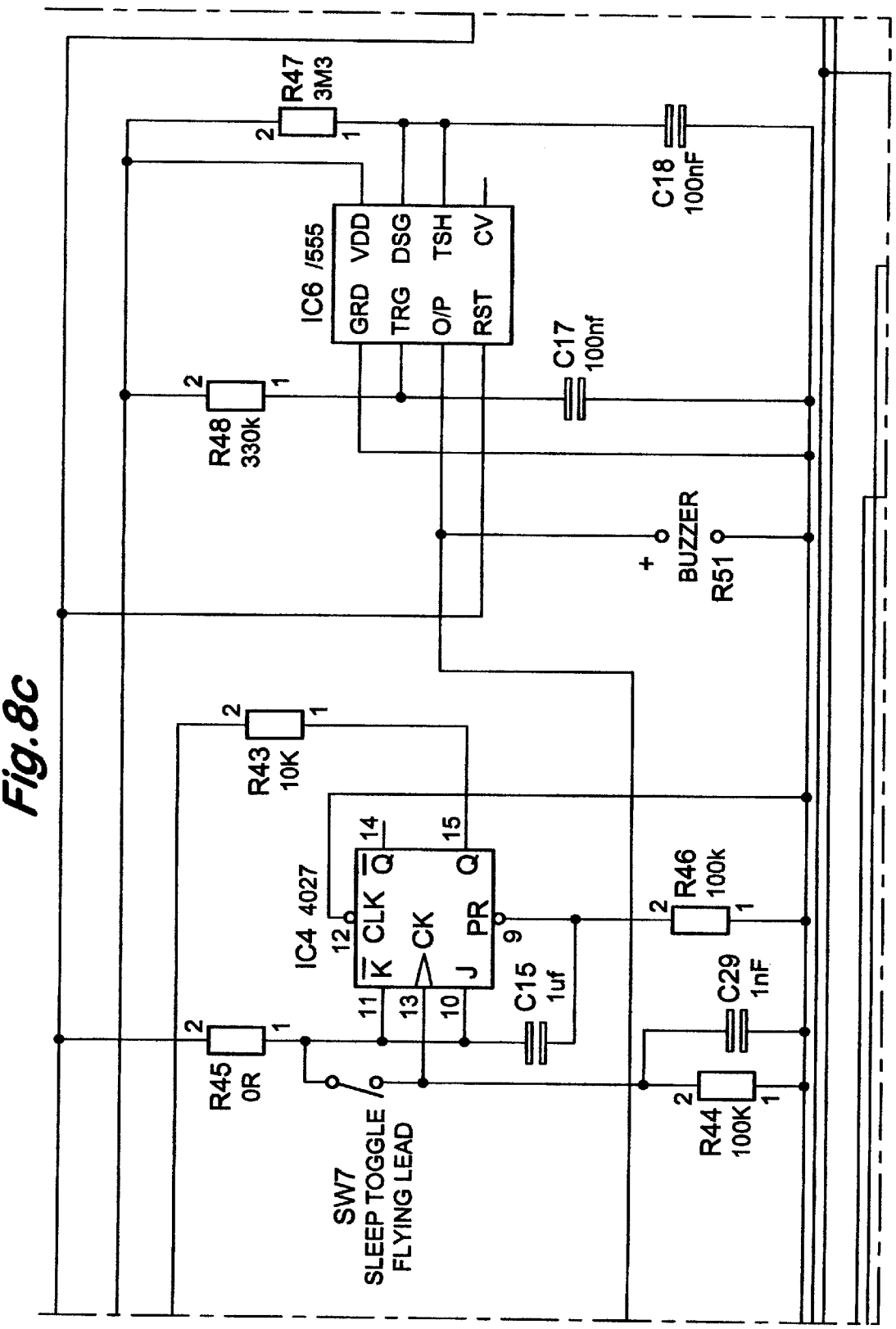
Figure 8D:
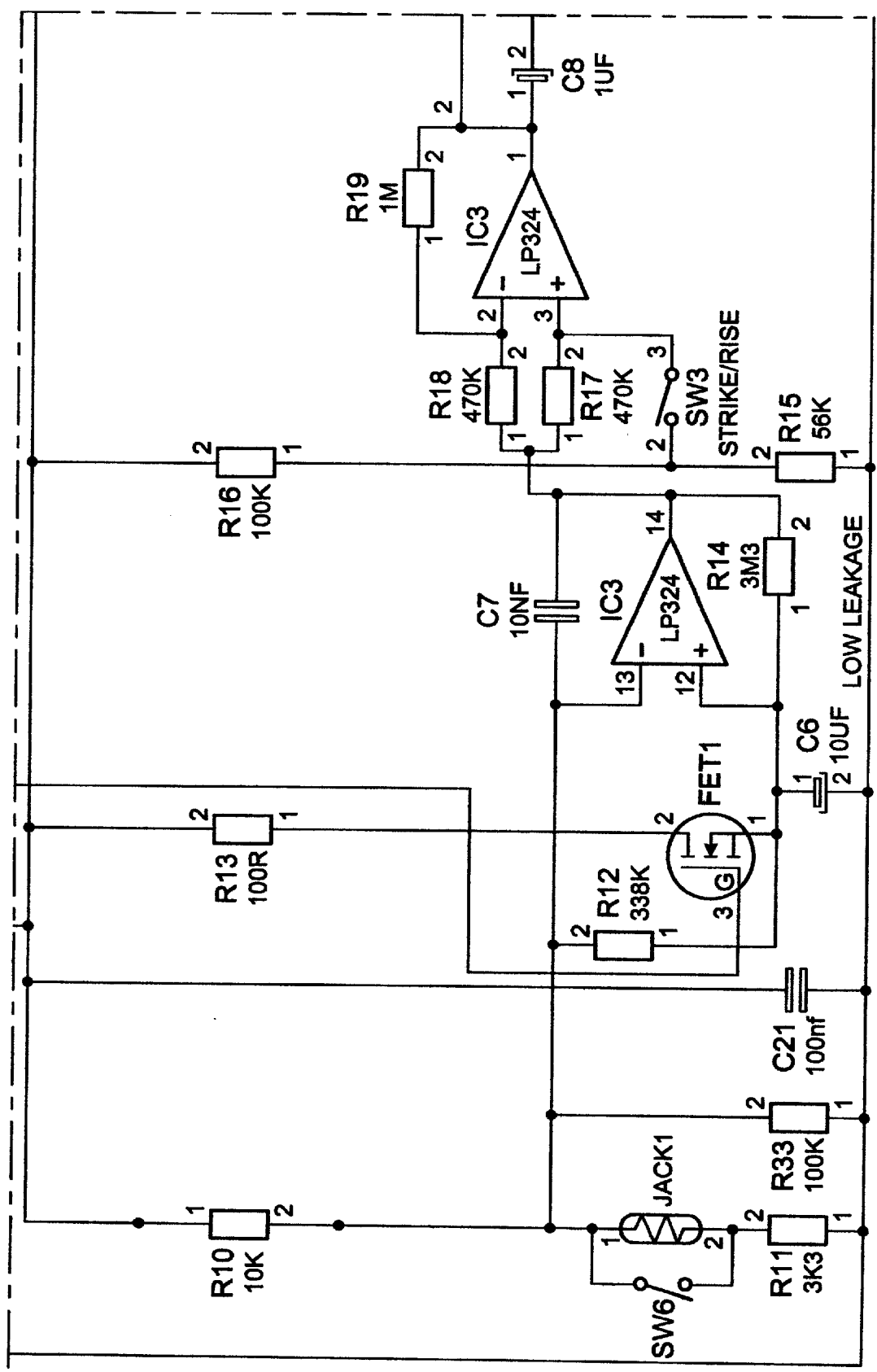
Figure 8E:
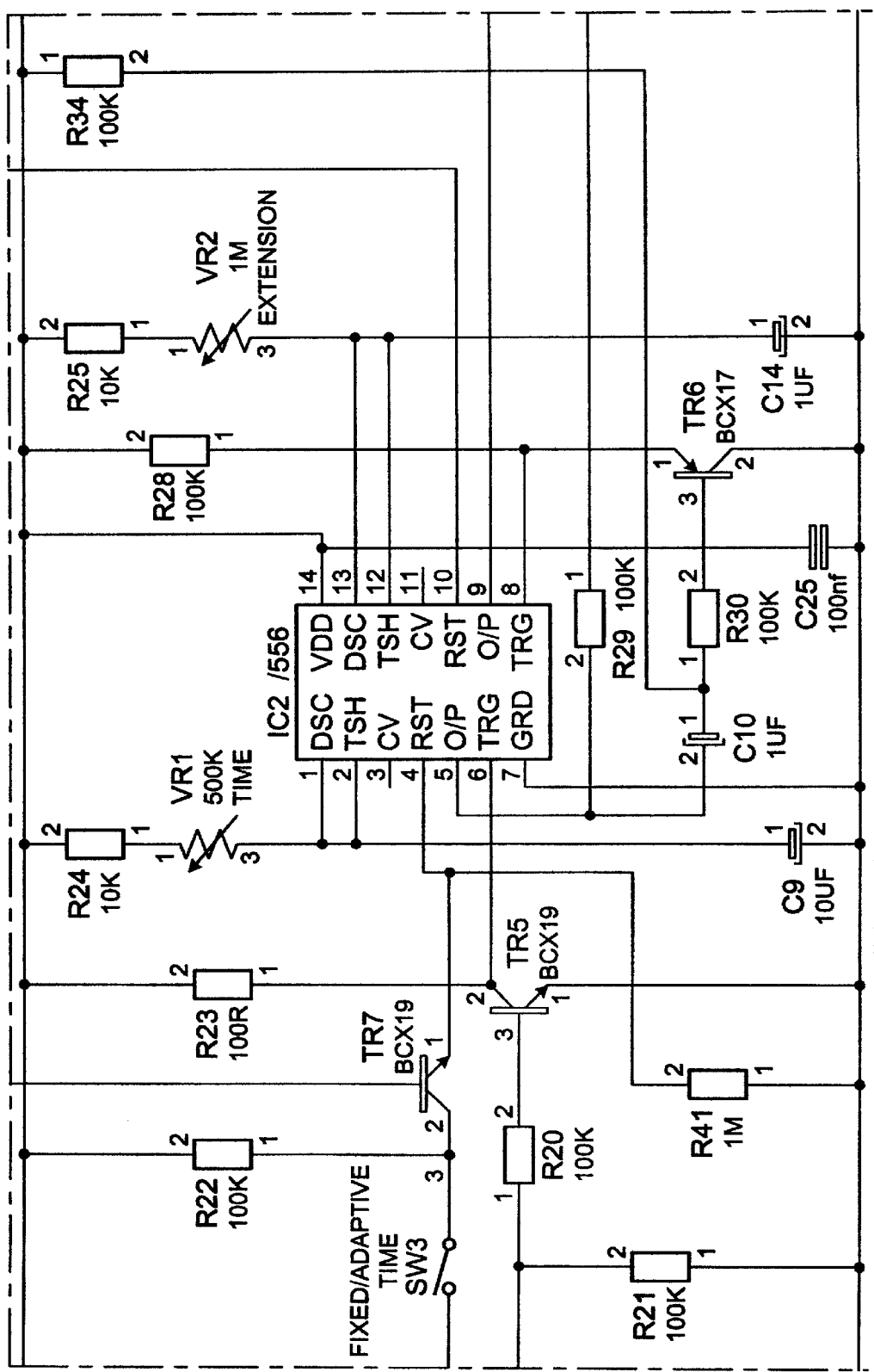
Figure 8F:
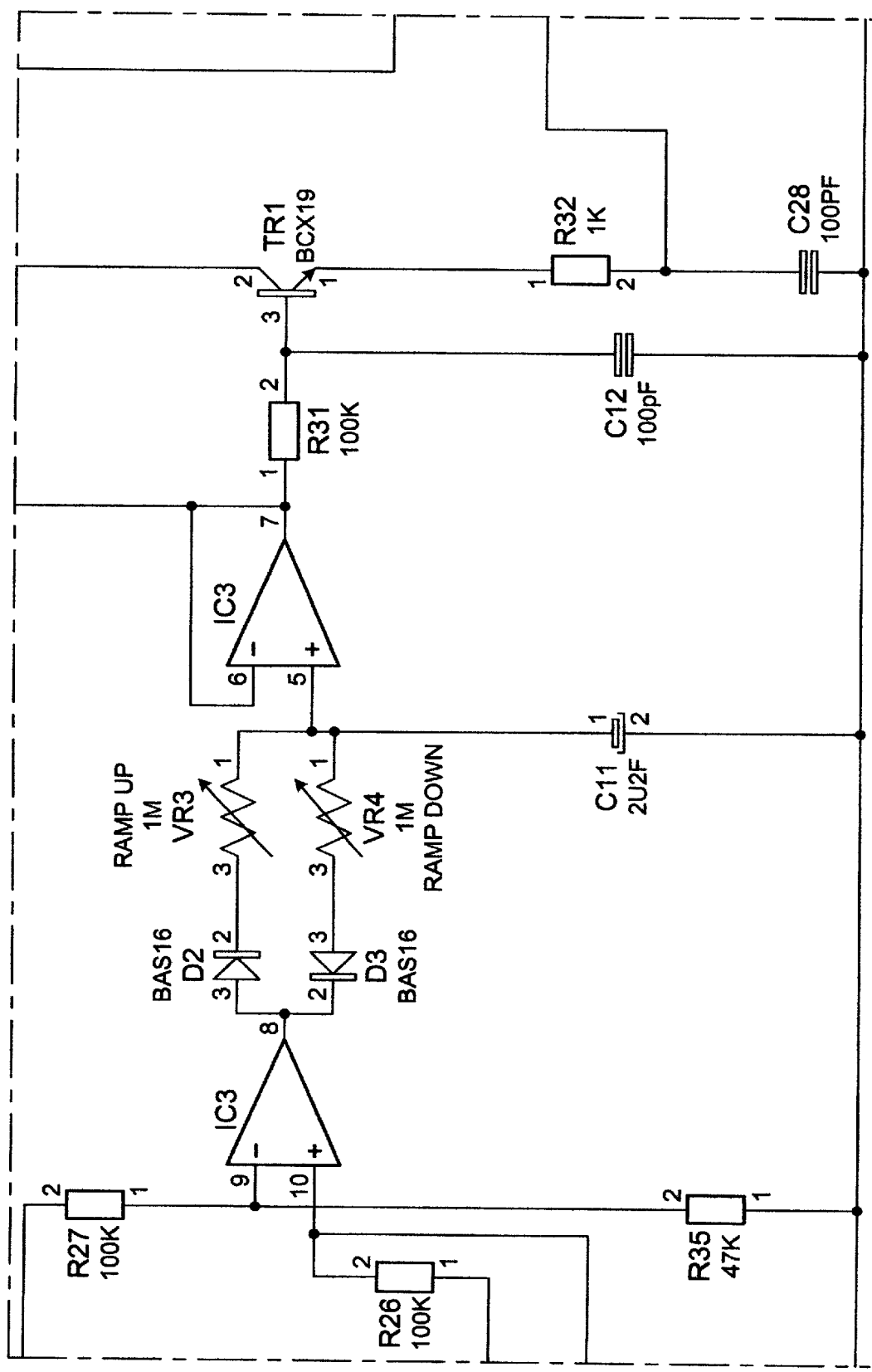
Figure 8G:
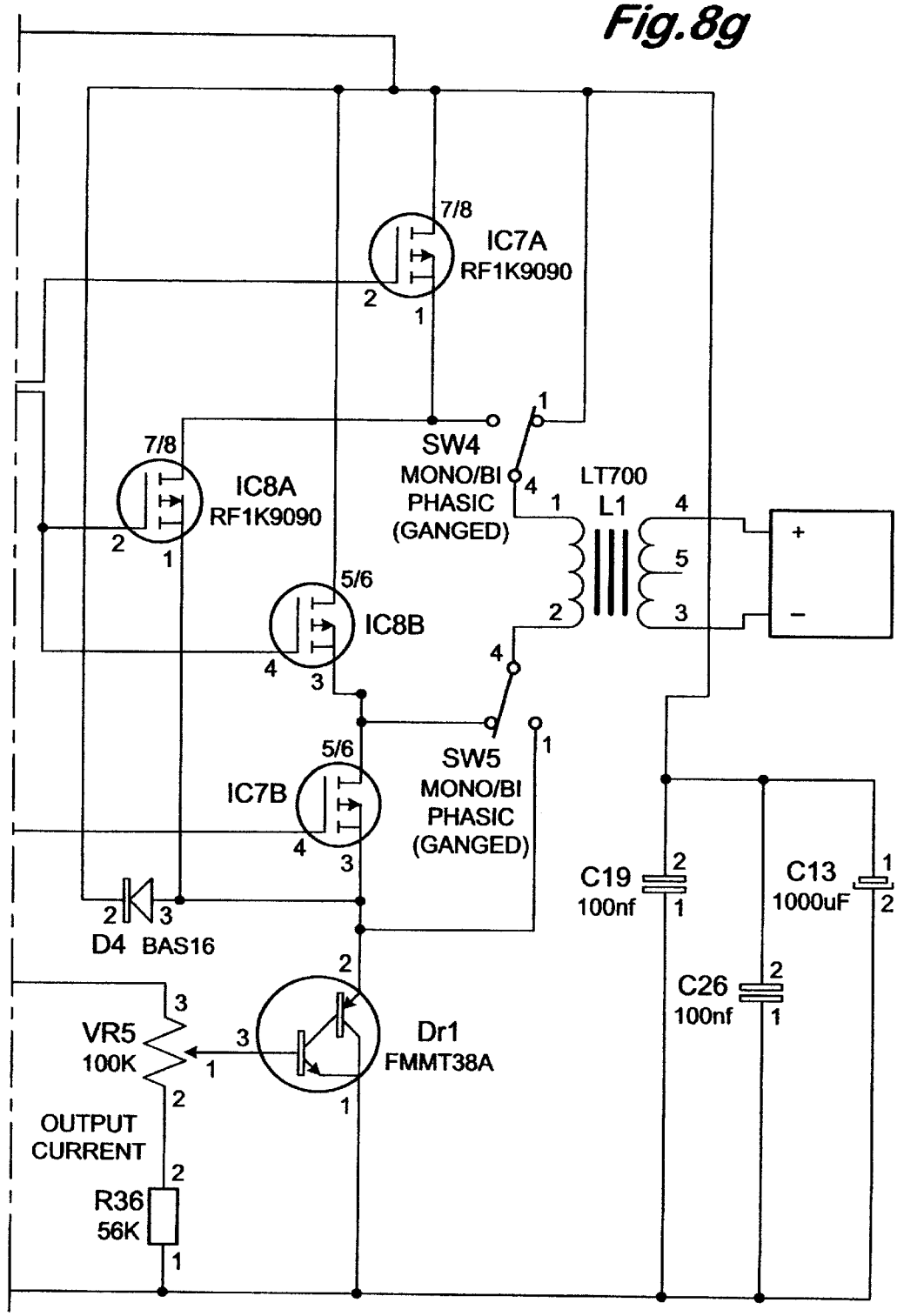

FIGS. 7a, and 7b combine together to form a block diagram showing the relationship between the foot switch 100, test button 102, and electrical waveform output stage 104 of the control circuit for the stimulation device. A tracking comparator 106 that adapts itself to the resistance of the foot switch 100 monitors the state of the foot switch and is also responsive to the test button 102.

When the driving circuit is first powered up via line 108, power is also fed to a state determination stage 110 that controls a flip-flop 112 to set the output of the flip-flop high. The output line 114 of the flip-flop 112 and the power line 108 are inputs to a transistor that provides an AND function 116. Also connected to the flip-flop 112 is a pause switch 118 that when closed causes the output of the flip-flop 112 to change state, in this instance from high to low so that the power to the circuit is removed. Subsequent operation of the switch 118 causes the flip-flop 112 to change state and returns power to the circuit. The user can therefore operate the switch 118 to discontinue application of electrical pulses to the nerve being stimulated for a desired arbitrary period, and can then operate the switch a second time to resume stimulation.

On initial power-up of the circuit or on re-energizing by actuation of the pause switch 118, the tracking comparator 106 is enabled within a period of about 0.5 seconds, and can then monitor the ON/OFF state of the foot switch 100. Power is fed to power-up trigger 120 and thence to a monostable 122 which provides a predetermined delay e.g. 0.5 seconds as indicated above, during which time a buzzer 124 is active to signal to the user that the stimulator is being energized. After the circuit has settled down, the tracking comparator 106 monitors the resistance of the foot switch 100 and automatically sets its operating threshold, as will be described more fully below.

The parts of the circuit described below construct the envelope of the signal applied to the user. The output of the comparator 106 is fed to an inverter/buffer 126 controlled by a switch 128 for actuation between a first state in which pulses are applied on heel rise and a second sate in which pulses are applied on heel strike. The clinician determines the setting when the apparatus is supplied to the patient, and the patient should not change it. The output signal from the buffer 126 passes to a trigger 130 that provides a single pulse either when pressure is applied to the switch 100 or when it is released. The trigger pulse passes to a first monostable 132 that is triggered for a preset maximum period that is normally set to be slightly longer than the swing phase of the user's gait. In this way the pulses are enabled or disabled for correct period during walking, and if the user stops walking to stand or to sit down, then after a short period of e.g. 2–3 sec stimulation automatically ceases. The output of the first monostable passes to a second mnonostable 134 that sets an extension period of e.g. 0.01–1.5 sec to produce an eccentric contraction of the tibealis anterior muscle, which mimics what happens in a normal physiological gait. Low-pass filters 136, 138 receive the output of the monostable 135 and shape the leading and the trailing edges of the stimulation envelope. The resulting signal passes via buffer 140 and mixer 142 to amplifier 144. A power-up delay unit 168 feeds its output to the monostables 132 and 134 to prevent them being triggered on power-up. Switch 170 when open provides a fixed period of monostable 132 and when closed provides an adaptive period which is terminated when the state of the switch 100 changes so the application of pulses to the nerve being stimulated is adapted to the speed at which the user is walking.

The pulses to be applied during the signal envelope are derived from bistable oscillator 146 whose output pulses which are typically of 200 microsecond duration and 40 pulses per second pulse rate are supplied to monostable 148 which provides variable length pulses which can be set (lengthened or shortened) by the user by means of a hand control and may typically be in the range 200–300 microseconds. The pulses from monostable 148 pass via low pass filter 150 to mixer 142 where they are combined with the envelope signal to provide an output waveform for amplifier 144. The output from the oscillator 146 passes via a low pass filter 152 to a flip-flop that controls a monophasic/biphasic MOSFET network 156 which may be by-passed on closure of a changeover switch 158. Output pulses pass via step-up transformer 160 via lines 104 to the active and indifferent electrodes. For visual feedback for the user and/or clinician, the output of the low pass feedback unit 152 passed via mixer 162 where it is combined with the envelope signal to amplifier 154 and thence to an LED 166. The brightness of the LED indicates pulses, and also the leading and trailing edge profiles of the envelope signal.

A practical circuit for implementing the above block diagram is shown in the combination of FIGS. 8a, 8b, 8c, 8d, 8e, 8f and 8g. The foot switch 100 is placed in a potential divider with R10 and R11. R11 prevents the potential divider voltage from dropping so low that the current through R14 becomes greater than that through R12. R33 emphasizes the lower end of the force sensitive resistor range. When the foot switch is pressed, the voltage on the switch input will vary continuously between about 8V and about 4V. Other switch types and the test button SW6 on the front panel causes the voltage to change abruptly between 8V and 4V. IC3/d is configured as a tracking comparator. The voltage from the switch input charges C6 through resistor R12 so that the voltage at the non-inverting input of ICs/d follows the voltage at the inverting input but with a delay corresponding to the time constant of R12 and C6. The voltage at the junction between R10 and footswitch 100 is applied to both inputs of IC3/d but with a time delay to the positive input IC3d therefore does not responsive to gradual changes in the resistance of the foot switch 100 as a result e.g. of wear or changes in humidity and temperature, but it will change state in response to a sudden change resulting e.g. from heel strike or heel lift. At switch on or when the apparatus enters its active mode following its sleep mode, the gate of FET 1 is taken high for about 0.5 s, causing C6 to be charged rapidly through R13. C6 is preferably a low leakage electrolytic capacitor. Ordinary electrolytic capacitors draw too much current through R14, causing the voltage difference across R12 to increase. When the voltage at the inverting input of IC3 is higher than the non-inverting input, the output is low. When the voltage at the inverting input is lower than the non-inverting input, the voltage is high. R14 provides hysteresis and C7 prevents oscillation.

The second integrated circuit IC3/a is configured as an inverter/buffer. When SW3 is open it acts as a buffer with unity gain. When SW3 is closed the non-inverting input is held at an artificial split rail voltage of about 3V by potential divider R15 and R16 and IC3/a acts as a unity gain inverter. In heel strike mode the voltage on pin 1 of IC3/a follows the switch input. In heel rise mode, the voltage is the opposite of the output. The output of IC3/a at pin 1 is split to provide two functions. One part is taken to the collector of TR7 and switch SW2 continues to the reset pin 6 of a first monostable IC2. TR7 acts as a gate, the signal from pin 1 of IC3/a being blocked when the base is low, which occurs momentarily at power up to prevent the monostable being triggered as the power rails rise. When SW2 is open the reset is pulled high by R22, whereas when SW2 is closed the reset follows the output from IC3/a pin 1, hence the monostable. The second part of the output from IC3/a pin 1 goes to C8 and R21, which act as a high pass filter, differentiating the output of the invertion/non-inverting amplifier. This produces positive and negative going spikes at the edge of the signal. The positive edges turn TR5 on, causing the voltage at the TRG terminal of TC2, pin 6, to momentarily fall from the power rail voltage. The voltage must fall to below ⅓ of the power rail voltage to trigger the monostable. TR5 protects IC1 from positive going spikes. R23 pulls the reset high when TR5 is turned off. If SW2 is open, the monostable is triggered and will run for as long as set by VR1, R24 and C9. If SW2 is closed, the monostable is triggered in the same way but will only run for as long as it is reset, pin 4 RST is held high or until the monostable times out. [Monostable time=1.1(VR1+R24)C9].

The output from the first monostable goes to a second monostable section to add the "extension" to the output signal. The extension section consists of two parts, a trigger and a monostable. The trigger differs from the previous trigger section as it produces a downward spike on the falling edge of the input from monostable 1. High pass filter C10 and R29 produces a positive going spike as the input goes high and a downward going spike as the input falls. PNP TR6 is turned off by the downward going spike and protects the input of IC2 from the positive going spike from the high pass filter which goes above the power rail. The monostable is triggered and will run as long as set by VR2, R25 and C14. As the reset is held high, the monostable will always run for a fixed time given by 1.1(VR2+R25)C14. The output passes through R26 where it is ORed with the input to the second monostable by R29. This point will be at the power rail voltage or at half the power tail voltage if both or either signals are high (R26 and R29 acting as a potential divider). The signal is fed to a comparator made around IC3/c at which it is compared with a voltage set by potential divider R35 and R27. The output of the comparator will be high whenever the non-inverting pin 10 is above threshold.

The output of the comparator is taken through two low pass filters made up from D2, VR3, C11 and D3, VR4 and C11. The capacitor C11 is charged through VR3 and is discharged through VR4 which ramps the output signal allowing the rising edge and the falling edge to be controlled separately. The outputs of the low pass filters are combined and fed to IC3/l that acts as a voltage follower and output buffer, preventing C11 from discharging into the next stage.

IC1 pins 1–6 produce the stimulation frequency and pulses to determine the LED rate and pulse width. Their rate is determined by R1, R37, R2 and C2. Diode D1 bypasses R37 and R2 when C2 is being charged. R1 determines the pulse width, which is given by 0.7×R1×C2 and may be set at e.g. 100 μs. R37 and C2 determine the inter-pulse interval, which is given by 0.7×(R37+R2)×C2 and may be set at 0.025 ms. IC1 pins 8–16 produce the stimulation pulse width. The output from IC1 pin 5 is differentiated by a high pass filter formed by C3 and R8, producing a positive-going signal that turns on TR2, causing the trigger input pin 8 of IC1 to momentarily drop low. The trigger input is held high by R4 when TR2 is off. The pulse width is determined by the front panel switch/potentiometer SW1, R3 and C25 and is given by 0.7×(SW1+R3)×C25. SW1 also disconnects the negative battery connection when moved to its off position, thus turning the apparatus off.

The stimulation pulse output passes through a low pass filter R49, C30 to reduce electromagnetic emissions and is mixed with the stimulation envelope signal and is applied to the base of TR1. Capacitor C12 shorts high frequency components in the signal from the pulse generator that would otherwise cause TR1 to become switched slightly on when the output is not triggered. The output signal passes through R11 and is attenuated by VR3 (positive going pulse). R36 sets the minimum level of output to about 15V assuming an output load of 1 kΩ in in parallel with a 100 μF capacitor. The signal from the wiper of VR5 supplies the base of a Darlington transistor Dr1, which acts as an amplifier with high current gain. With negative going pulses the input to the transformer is normally high.

The emitter of DR1 feeds a transformer via ganged switches SW4 and SW5. The transformer provides voltage gain and isolates the output from the remainder of the electronics. When the ganged switches by-pass FETs IC7 and IC8, the output is mono-phasic. When the FETs are switched in, the Q and Qbar outputs of IC4a turn on IC7a and IC7b alternately with IC8a and IC8b. IC4a is a JK flip-flop configured as a divide by 2 toggle and is clocked by the output from the bistable IC1 pin 5. D4 acts as a fly-back diode to prevent EMF from damaging DR1. The output from the transformer is connected to the active and indifferent electrodes.

C13 acts as a reservoir capacitor smoothing the output stage power rail. The power rail for the timing electronics is smoothed separately by C16 and is isolated from the output stage power rail by TR8. D7 protects the circuit from incorrect battery insertion.

TR8 is turned on via R43 by the Q output of the flip-flop divide by two toggle of IC4b. At power up, R46 and C15 ensure that the PR pin 9 input is momentarily low while the CLR pin 12 is high, setting the flip-flop so that Q pin 15 is always high, and ensuring that the apparatus is always in its active mode when switched on. R44 pulls the CK pin 13 input low, while C29 provides switch de-bouncing for the push buttons SW7 mounted on the side of the apparatus, IC5 provides a momentary low at power-up. R38 and R40 provide a reference for the comparator. C5 is charged through R39, causing the output of the comparator to be low until it passes a threshold set by R38 and R40. The output is used as a reset for IC2b and gates the reset signal of IC2a via R9 and TR8. This ensures that the rising power rail voltages at switch on cannot trigger the monostables.

The LED is driven by Tr4 with a signal derived by mixing the bistable output from IC1a pin 5 (via a low pass filter R53, C1 to reduce electromagnetic emissions) and the stimulation envelope signal from IC3 pin 7 by R6 and TR3. The monostable IC6 provides drive to the buzzer and to FET1. On power-up C17 is charged through R48, causing a momentary low voltage at the TRIG input, triggering the monostable, which then runs for a time set by C18 and R47.

Although a single channel stimulator can significantly improve the mobility of many patients with dropped foot, there is a clinical need in some individuals to improve the control of the knee, hip and ankle joints due to lack of or inappropriate muscle activity. In addition there are many subjects who have bilateral dropped foot due to cerebral palsy, multiple sclerosis or familial paraplegia. The need to control additional muscle groups can be met, according to a further aspect of the invention, by a two-channel stimulator in which active and indifferent electrodes of the second channel are applied at loci that are effective to control the required muscle groups.

Figure 9:
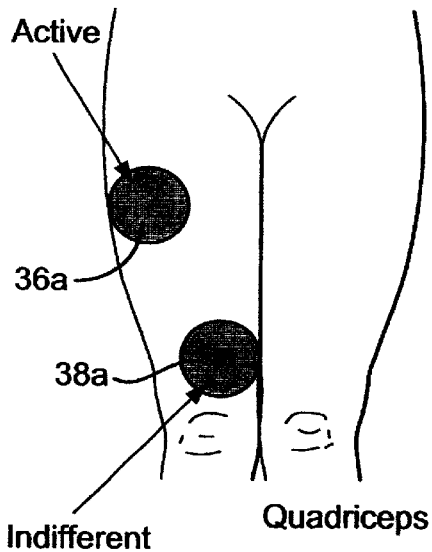
FIG. 9 is a partial front view of a user showing electrode attachment positions for stimulation of the quadriceps.

FIG. 9 shows active and indifferent electrodes 36a, 38a applied to the calf of a user's leg to stimulate the quadriceps muscle. The active electrode 36a of the second channel is placed midway up he thigh and about 5 cm to the outer (lateral) side. If the active electrode is placed too close to the center of the thigh, the rectus femoris muscle is stimulated causing hip flexion. The indifferent electrode 38a is placed just above the knee and slightly to the inside of the leg. Stimulation causes the knee to straighten.

Figure 10:
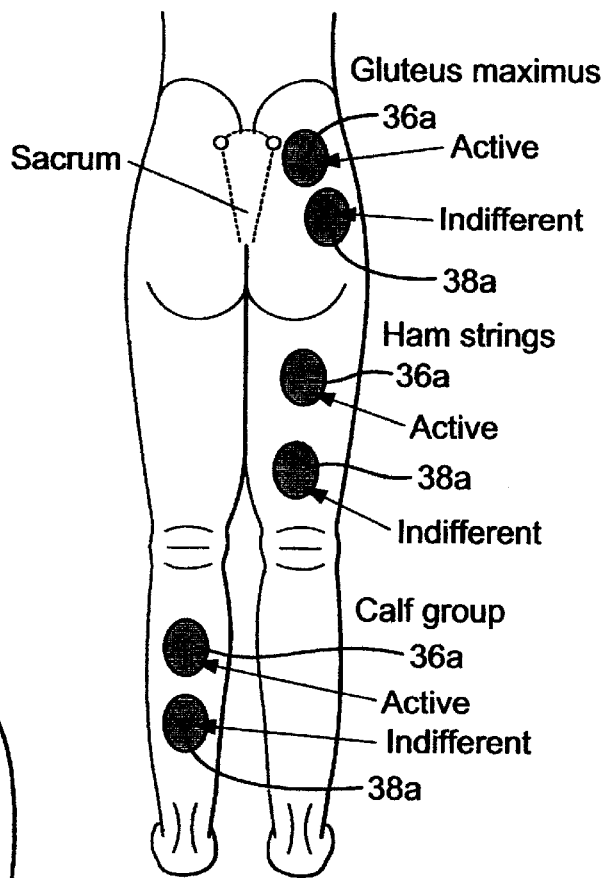
FIG. 10 is partial rear view of a user showing electrode attachment positions for stimulation of the gluteus maximus, hamstrings and calf muscle.

FIG. 10 shows the lower portion of the user's body with various positions for attachment of second channel electrodes.

For stimulation of the gluteus maximus, the active electrode 36a is placed just below the dimples at the top of the sacrum and the indifferent electrode is placed approximately a hand's breadth below the active electrode and approximately level with the cocyx. Stimulation causes the hip to be extended. If the electrodes are positioned too far in a lateral direction, the gluteus medius may be stimulated, causing hip abduction. If the indifferent electrode is placed too low, the hamstrings may be stimulated, causing knee flexion.

For stimulation of the hamstrings the indifferent electrode 38a is placed just above the back of the knee and the active electrode 36a is placed over the centre of the muscle about two hand widths above the indifferent electrode.

For stimulation of the calf muscles the active electrode 36a is placed just above the widest part of the calf muscle and the indifferent electrode is placed towards the bottom of the calf muscle.

Figure 11:
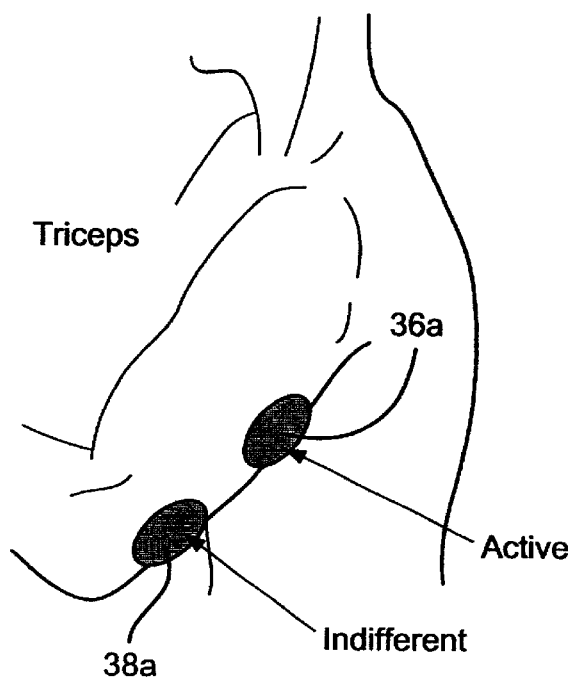
FIG. 11 is a partial side view of a user showing electrode positions for stimulus of the triceps.
Figure 12A:
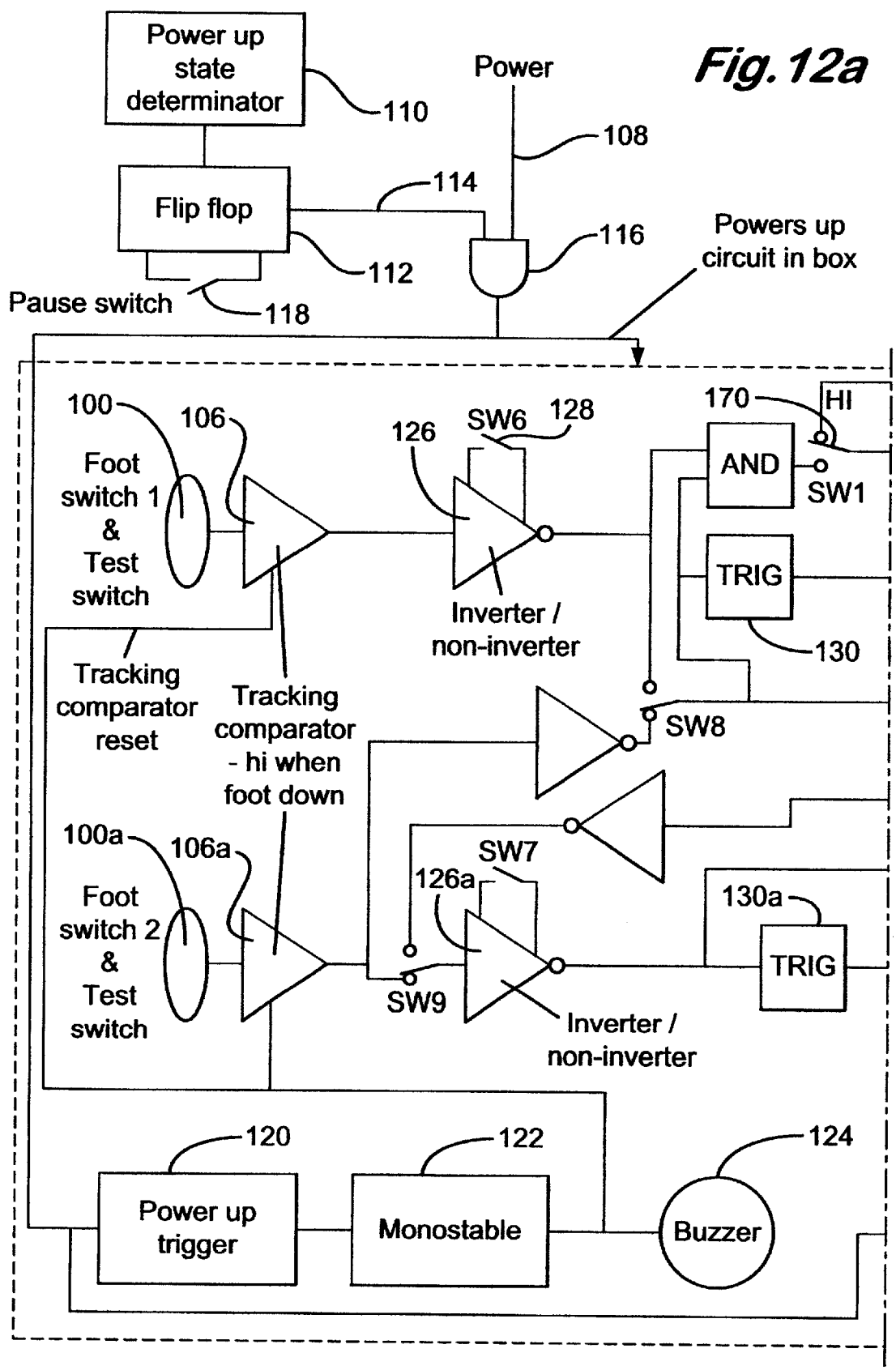
Figure 12B:
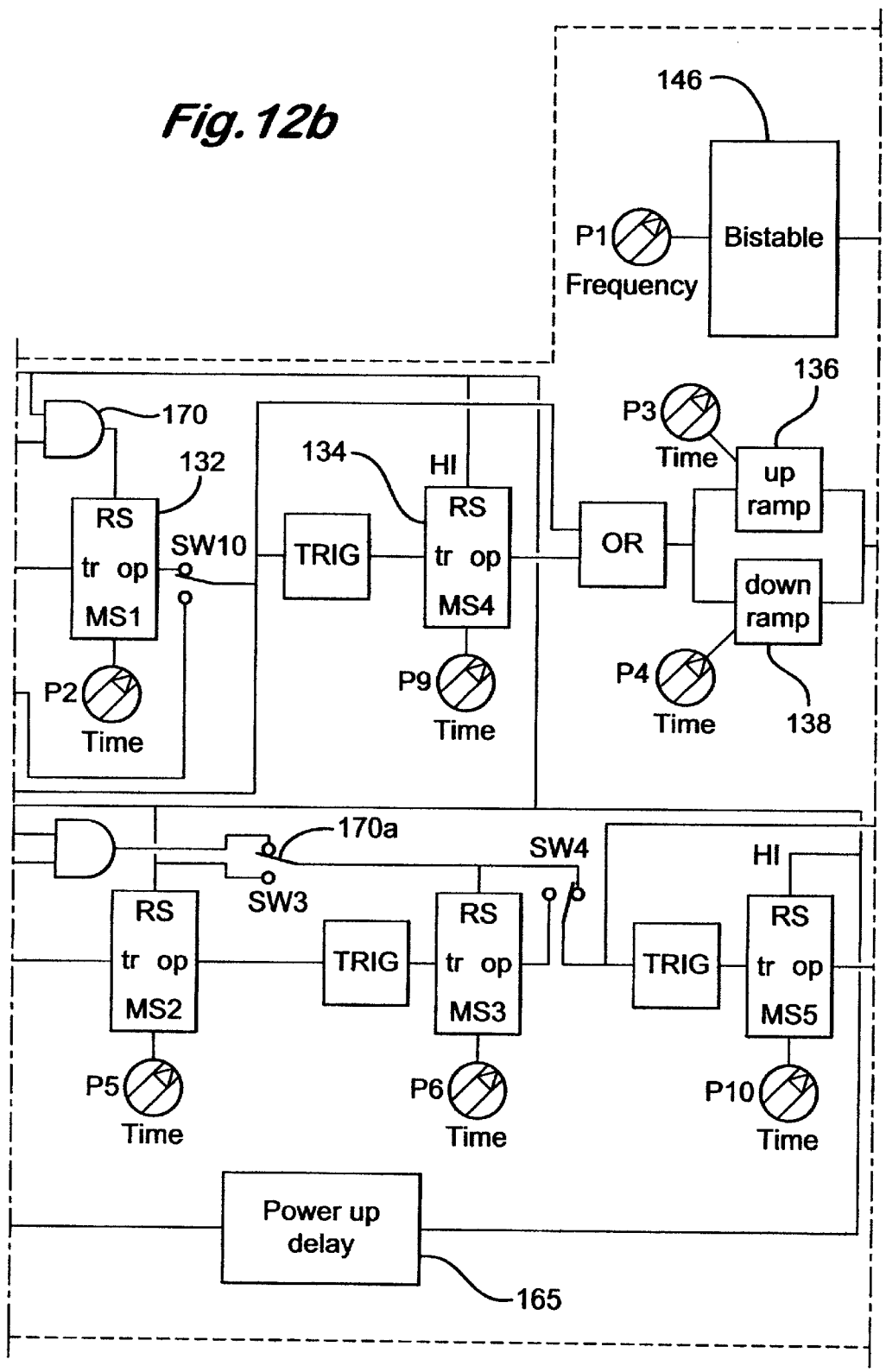
Figure 12C:
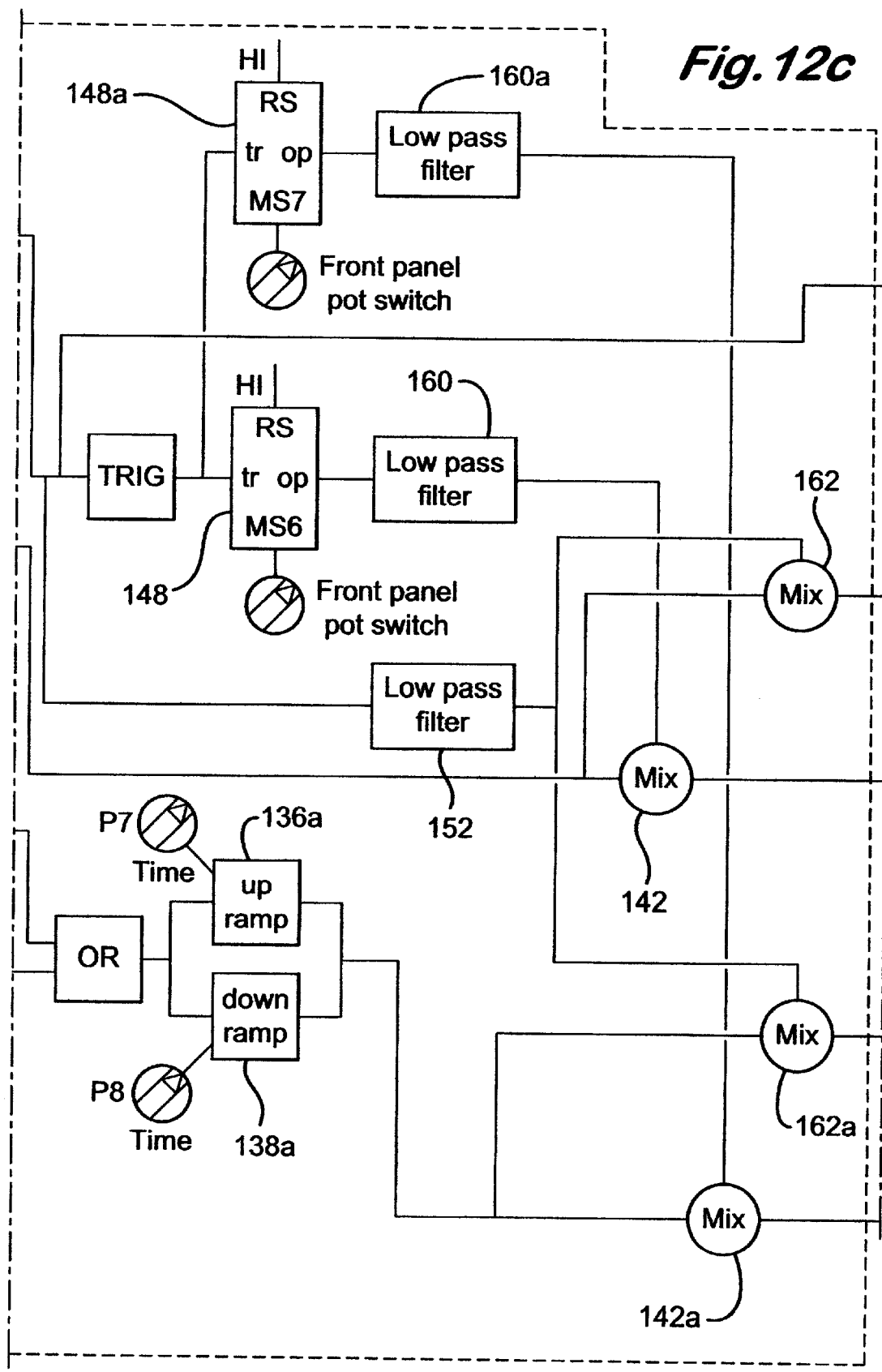
Figure 12D:
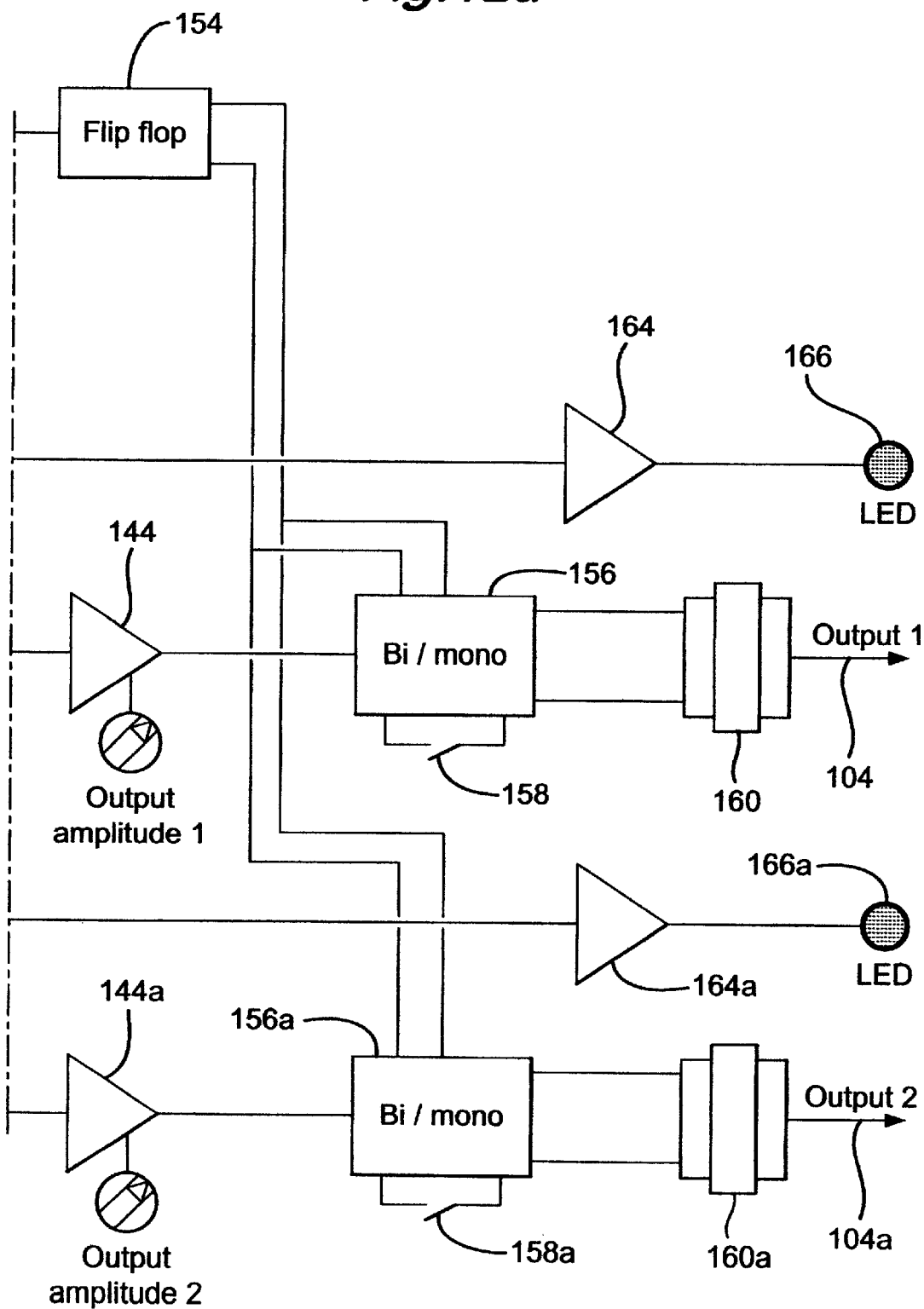

FIG. 11 shows the second electrodes located for stimulation of elbow extension. For that purpose the active electrode 36a is placed over the center of the triceps and the indifferent electrode is placed just above the elbow.

Various algorithms may be used to treat different patient conditions with stimulation of different groups of muscles during the gait cycle. Commonly seen abnormal gait patterns that may be improved by stimulating a second muscle group include:

Bilateral foot drop

Ineffective push-off

Abnormal knee control and movement

Pelvis and hip-joint problems

Associated reactions in the arm.

When considering which muscle groups to stimulate and when, it is necessary to consider (a) the direct effect of stimulation to bring about muscle contraction and (b) the inhibitory effect on the antagonist muscle group. When planning the appropriate pattern of stimulation for a user it should be remembered that the functions that can be produced by electrical stimulation are not the same as natural patterns of movement, which typically involve several muscles and reflex activity. Therefore if electromyograph measurements show that a particular muscle is active at a given point in the gait cycle, it does not follow that functional electrical stimulation at the same point in the gait cycle will produce the same effect. Furthermore, there is a delay between electrical stimulation and the production of muscle force that becomes increased where, as in common peroneal stimulation, a reflex is involved. Examples of algorithms that can be used are given below:

Bilateral dropped foot: A single heel switch may be used with channel 1 being triggered by heel rise and ended by heel strike and channel 2 triggered by heel strike after a short delay and ended by heel rise. The link between the two channels prevents both of them from being active simultaneously which could put the user into an unstable condition.

Dropped foot with ineffective push-off. The effects of minimal plantarflexion at push-off are that (a) the heel and the toe leave the ground almost simultaneously, (b) the body does not move forward over the base of support during the stance phase of walking and (c) acceleration at toe lift is lost. In addition to correction of the dropped foot, the user's walk may be further improved by stimulation of the calf during mid to late stance. A heel switch may be used and a toe switch may be located under the first metatarsal. Channel 1 may be used for common peroneal stimulation which may be triggered by toe-off and which may be ended either by heel strike or by toe strike. Channel 2 stimulates the calf muscle and is active while the toe switch is on the ground up to a maximum or time-out period.

Bilateral ineffective push-off. Channels 1 and 2 are used to stimulate the two calf muscles and may be controlled by toe switches for each foot. No interaction between the channels is required.

Dropped foot with hyperextension during the stance phase. Hamstring stimulation may be used to inhibit knee hyperextension and as a sensory stimulus to improve perception of knee position. Control may be based on a single heel switch or on heel and toe switches as in the previous example. Common peroneal stimulation may be triggered by heel rise and ended by heel strike. Hamstring stimulation may be triggered with a predetermined delay in response to either heel strike or toe strike. Hamstring stimulation may also be used on initial heel contact to control knee hyperextension, during the swing phase to enhance knee flexion and during the stance phase to break spasm of the quadriceps.

Dropped foot with failure to achieve sufficient knee extension during the terminal part of the swing phase and during the stance phase. Quadriceps stimulation may be used during the terminal part of the swing phase and during stance to improve support in the stance phase. Control may be based on a single heel switch, with common peroneal stimulation in channel 1 as in the previous examples and with quadriceps stimulation in channel 2 for as long as the heel switch is subject to pressure (i.e. channel 2 does not time-out and stimulation of the quadriceps continues while the patient is standing still). Quadriceps stimulation may also be initiated during the swing phase to improve braking of the leg Bilateral failure to achieve sufficient knee extension during terminal swing phase and during stance. Two heel switches control the two channels and no interaction between them is required. Both channels give an output at heel strike and while the heel switch is subject to pressure.

Dropped foot with insufficient hip extension. Channel 1 is used to provide common peroneal stimulation as before and channel 2 is active between heel contact and heel rise to stimulate the gluteus maximus.

Dropped foot with inadequate arm swing. As some patients walk the arm takes up a flexed position and rythmic arm swing is lost, with consequential effects on balance. Improvements may be achieved by stimulating the triceps and posterior deltoid muscles using the same period as the common peroneal stimulation, but with a longer ramp to avoid eliciting a stretch reflex in the biceps. Both channels are controlled by a single heel switch, with common peroneal stimulation as above and with synchronous triceps stimulation.

The facilities that it is desirable to provide in a two-channel stimulator include the following:

A delay facility for the output of the second channel, which allows signals in the second channel to be synchronised with the gait cycle.

Time-out disable. The single channel embodiment described above has a time-out facility so that e.g. if the user sits down, lifts his heel from the ground and does not return his heel to the ground, although the circuit is in heel-rise mode a continuous output is not given. As explained above, it may be desirable in the second channel to provide for continuous output e.g. for stimulation of the quadriceps during weight bearing. In timeout disabled mode, channel 2 maintains its output until the foot switch changes state.

Single input interactive control. A single foot switch e.g. for channel 1 may be used to control both channels, the foot switch for channel 2 being absent or disabled. Channel 2 is triggered either by the start (rise) or the end of the output from channel 1.

Interactive control with dual inputs. This permits the stimulus in one of the channels to be started by a change of state in the first switch and to be ended by a change of state in the second switch, the second channel being controlled independently in response to the state of one of the switches.

FIGS. 12a, 12b, 12c, and 12d combining together to form a block diagram of a two-channel nerve stimulator, in which components having essentially the same functions as those of the single channel version of FIGS. 7a and 7b have the same reference numerals, those in the second channel being identified by the added letter a. Channel 1 is arranged to respond to the state of footswitch 100 and also to the state of footswitch 100a so that it can be started by the footswitch 100a of the second channel and stopped by the footswitch 100 of the first channel. SW 8 provides this function because in its up position channel 1 is entirely controlled by footswitch 1, whereas in its down position supply of stimulation pulses in channel 1 is started by the footswitch 100a of channel 2 and ended by the footswitch 100 of channel 1. SW 10 enables monostable 132 which provides the time-out in channel 1 to be by-passed e.g. for continuous stimulation of the quadriceps muscle for support. SW9 enables channel 2 to be controlled either by the footswitch 100 of channel 1 or by its own footswitch 100a. For that purpose it either passes the inverted output of monostable 132 (inversion is to avoid change in the meaning of the switch SW7 when the state of switch SW9 is changed) or the output of the tracking comparator 106a. Channel 2 is controllable either directly from footswitch 2 or the output of a monostable 132. The output of that monostable is high when channel 1 is active.

In channel 2 the monostable MS2 provides delay and the monostable MS3 provides the main output envelope. SW3 enables fixed or adaptive timing—when it is up the reset of MS3 is controlled by the input to channel 2 and when its down its output is held high by the power up circuitry and the monostable remains high as long as the input is high until MS3 times out. SW4 has the same function as SW10 in channel 1 and enables MS3 to be by-passed so that the output envelope is simply controlled by the state of the foot switch 100a. Monostables MS 6 and MS7 provide the signal pulse durations for channel 2 and are triggered by a common bistable 146 so that each channel can provide reproducible pulse intensity under a range of operating conditions.

The force-sensitive resistors, which are used in both the single-channel and the two channel embodiments of the above stimulation apparatus, need to be reasonably stable after high numbers of operations under the adverse conditions encountered when they are fitted e.g. to an insole of a user's shoe. FIGS. 13a–13g show successive stages in the manufacture of a switch that has in practice been found to achieve the required level of stability and performance. The combination of a resistive switch as described below and the adaptive circuits described above can achieve the required level of overall reliability for wide acceptance by users.

Figure 13A:
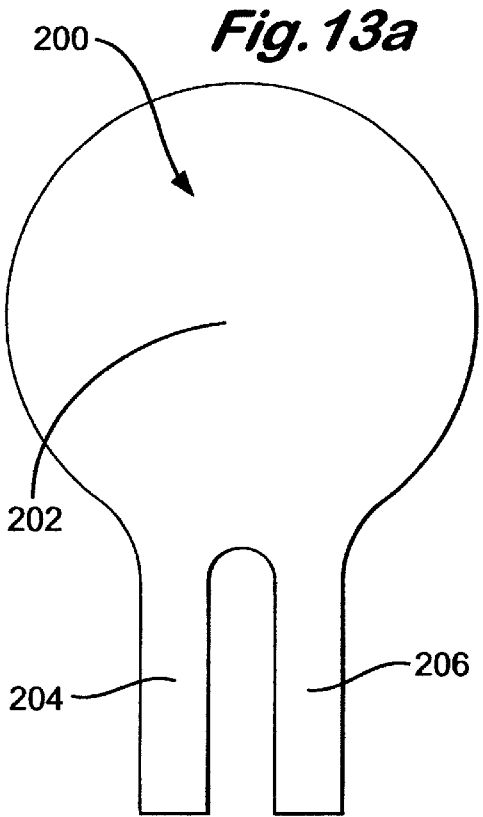
Figure 13B:
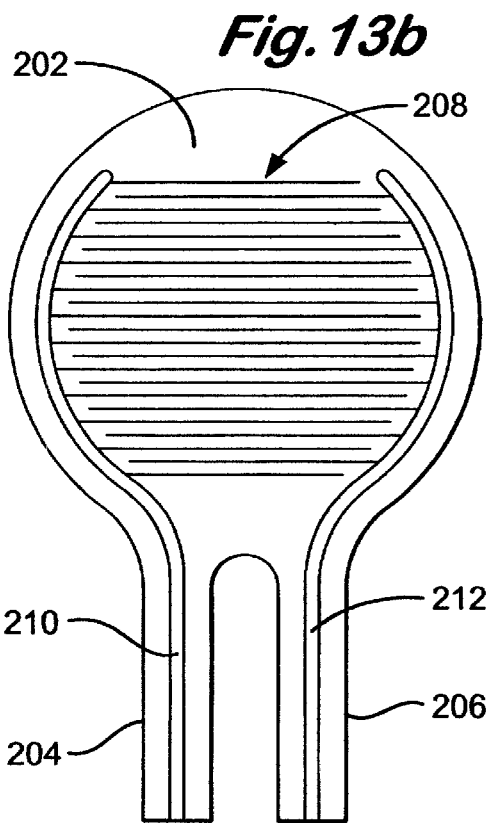
Figure 13C:
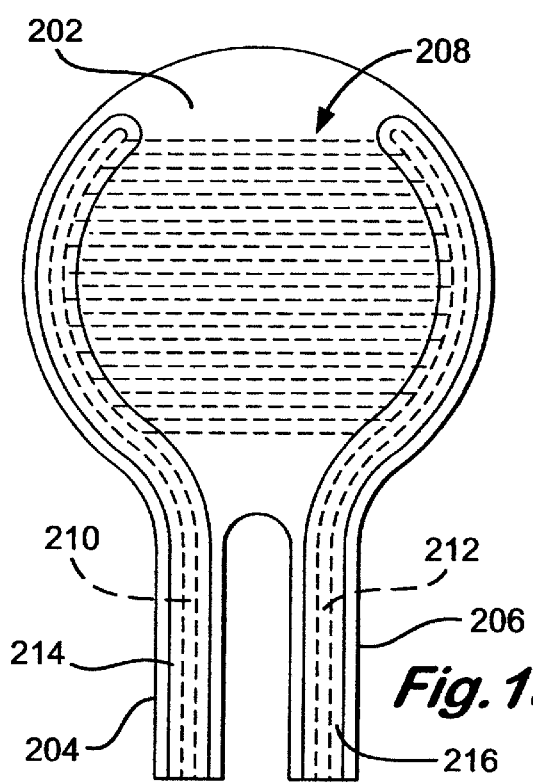
Figure 13D:
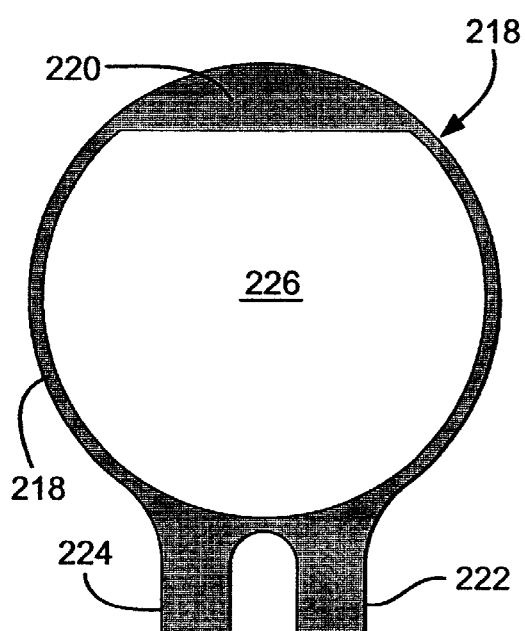

In FIG. 13a, the first part of a resistive switch is made starting from an insulating plastics sheet 200 is formed with a head region 202 of diameter typically about 25–30 mm and lead-defining extensions 204, 206 of length typically about 15 mm and of width typically about 2.5 and 3 mm. The sheet 200 is printed with an ink that leaves a conductive metallic pattern e.g. of silver that defines an inter-digitated array 208 connected to leads 210, 212 as shown in FIG. 13b. The leads 210 and 212 are relatively narrow where they provide connections to the individual non-contacting fingers of the two portions of the array 208, but widen along the extensions 204, 206. The leads are over-printed with a carbon-based ink to leave carbon over-layers 214, 216 that cover the leads 212,214 and have the same overall shape but are slightly wider as shown in FIG. 13c. The over-printing is believed to increase the life of the switch and to reduce the risk of damage due to e,g. sweat or other moisture ingress. The second part of the resistive switch is shown in FIG. 13d and comprises a plastics sheet 218 having a head 220 conforming to the head 202 of the first switch part, and having stub projections 222 and 224 for covering a proximal region of the extensions 204,206. One face of the sheet 218 carries a layer 226 of semiconductive material having a lower surface with a texture or roughness or content of conductive material such that when pressed against the electrodes of the array 208 they form an connection between the fingers of the opposed sides of the array 208 that decreases with applied pressure. An adhesive layer 228 on the same face of the sheet 218 as the semiconductive layer 226 surrounds the layer 226 and extends along the stub projections 222 and 224. To complete the active part of the switch the adhesive face of the sheet 218 is offered up to the conductor-bearing face of the sheet 200 to complete the sub-assembly of FIG. 13e in which portions of the leads 210,212 and carbon over-layers 214,216 project beyond the stub projections 222,224.

The operations of finishing the switch are shown in FIG. 13f. The ends of cable 230 are stripped to expose the tinsel wires 232 and 234 within them. Heat shrink sleeves are passed over the tinsel wires, after which the tinsel wires are adhered to the over-layers 214, 216 by means of conductive epoxy adhesive 240, 242. After the adhesive has set, the sleeves 236,238 are slid into register with the joints that have just been made and shrunk e.g. using a hot air gun. The joint is then potted e.g. with a thin layer of an epoxy resin 244, and any surplus potting material is trimmed. The open-circuit resistance may be tested at this stage and may typically be 100 KΩ with no load applied, falling below about 5 m when the switch is pressed. A label 246 carrying a serial number is then placed onto the switch and the head region has adhered thereto e.g. by double sided adhesive tape discs 248,250 of Poron or other shock-absorbent material. Poron is a cellular polyurethane available from Rogers Corporation, USA. The assembly is then heatsealed into inner and outer pouches 248, 250 of transparent plastics material,

What is claimed is:

1. A functional electrical stimulator for attachment to the leg comprising:
   first and second electrodes for attachment to the leg to apply an electrical stimulus;
   a foot switch for sensing foot rise or foot strike;
   a circuit responsive to said foot switch for generating stimulation pulses; and
   means forming part of said circuit for responding to changes in the resistance characteristics of said switch means by adjusting a corresponding response threshold of said circuit.

2. The stimulator of claim 1, wherein the foot switch comprises a force-sensitive resistor.

3. The stimulator of claim 2, wherein the value of said resistor reduces from a maximum of about 2 MΩ to a minimum of about 2 kΩ when force is applied to it.

4. The stimulator of claim 1, wherein the circuit comprises a tracking comparator having a potential divider of which the foot switch forms part, a capacitor for providing a reference voltage, and a resistor connected to the potential divider for charging the capacitor to provide said reference voltage.

5. The stimulator of claim 1, wherein the circuit has means providing a sleep mode, and means for establishing the reference voltage rapidly when the apparatus is switched on or taken out of sleep mode.

6. A method of treating drop foot of a user utilizing the electrical stimulator of claim 1 comprising the steps of:
   attaching the first and second electrodes to the leg of the user;
   sensing foot rise and foot strike with the foot switch;
   generating stimulation pulses with the circuit responsive to the foot switch; and
   responding to changes in the resistance characteristics of the foot switch by adjusting the corresponding response threshold of the circuit responsive to the foot switch.

7. An electrical stimulator for attachment to the body comprising:
   first and second electrodes for attachment to the body to apply an electrical stimulus;
   pressure switch means which goes between on and off states on application and removal of load;
   a circuit responsive to said pressure switch means for generating stimulation pulses; and
   means forming part of said circuit for responding to changes in the resistance characteristics of said pressure switch means by adjusting a corresponding response threshold of said circuit.

8. Electrical apparatus for connection as part of a functional electrical stimulator for the leg, said apparatus comprising:
   means providing a removable connection for first and second electrodes that in use are attached to the leg to apply an electrical stimulus;
   means providing a removable connection for a foot switch for sensing foot rise or foot strike;
   a circuit for responding to said foot switch for generating stimulation pulses; and
   means forming part of said circuit for responding to changes in the resistance characteristics of said switch by adjusting a corresponding response threshold of said circuit.

9. An electrical stimulator for attachment to the body comprising:
   first and second channels for supplying stimuli to discrete muscle groups, each channel having first and second electrodes for attachment to the body to apply an electrical stimulus to a respective muscle group and a circuit for supplying stimulation pulses to said electrodes;
   at least one switch means responsive to limb position for controlling the supply of stimulation pulses in at least one channel; and
   means defining a signal pathway between the first and second channels so that the supply of stimulation pulses in one of said first and second channels can be controlled by the state of switch means associated with the other of said first and second channels.

10. The stimulator of claim 9, wherein supply of the stimulation pulses via the first channel is arranged to be initiated by change in state of a switch associated with the second channel and is arranged to be ended by change in state of a switch associated with the first channel.

11. The stimulator of claim 9, wherein the at least one switch means comprises a pressure-sensitive resistor.

12. An electrical stimulator for attachment to the body comprising:

first and second channels for supplying stimuli to discrete muscle groups, each channel having first and second electrodes for attachment to the body to apply an electrical stimulus to a respective muscle group and a circuit for supplying stimulation pulses to said electrodes;

at least one switch means responsive to limb position for controlling the supply of stimulation pulses in at least one channel; and means defining a signal pathway between the first and second channels so that the supply of stimulation pulses in one of said first and second channels can be controlled by the state of activity of the other of said first and second channels.

13. The stimulator or claim 12, wherein change in state of switch means associated with the first channel is arranged to initate supply of the stimulation pulses in the first channel, and the signal pathway between the channels includes delay means so that supply of pulses in the first channel initiates supply of pulses in the second channel with a delay.

14. An electrical stimulator for attachment to the body comprising:

first and second channels for supplying stimuli to discrete muscle groups, each channel having first and second electrodes for attachment to the body to apply an electrical stimulus to a respective muscle group and a circuit for supplying stimulation pulses to said electrodes; at least one switch means responsive to limb position for controlling the supply of stimulation pulses in at least one channel; and means for controlling the supply of stimulation pulses in the second channel, said means being selected from (a) second switch means which changes state on the application of pressure and (b) connections to the first channel for supplying to said second channel a signal indicative of the state of the first channel.

15. An electrical stimulator for attachment to the body comprising:

first and second channels for supplying stimuli to discrete muscle groups, each channel having first and second electrodes for attachment to the body to apply an electrical stimulus to a respective muscle group and a circuit for supplying stimulation pulses to said electrodes;

at least one switch means responsive to limb position for controlling the supply of stimulation pulses in at least one channel;

the first channel having means arranged to cause the stimulation pulses to time-out after a predetermined period.

* * * * *